US012090272B2

(12) United States Patent
Higashiyama et al.

(10) Patent No.: US 12,090,272 B2
(45) Date of Patent: *Sep. 17, 2024

(54) CONTINUOUS POSITIVE AIRWAY PRESSURE APPARATUS

(71) Applicant: Murata Manufacturing Co., Ltd., Nagaokakyo (JP)

(72) Inventors: Yuzo Higashiyama, Nagaokakyo (JP); Hiroaki Wada, Nagaokakyo (JP); Shigeru Tsuji, Nagaokakyo (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/493,150

(22) Filed: Oct. 24, 2023

(65) Prior Publication Data

US 2024/0050673 A1 Feb. 15, 2024

Related U.S. Application Data

(63) Continuation of application No. 17/023,914, filed on Sep. 17, 2020, now Pat. No. 11,833,300, which is a
(Continued)

(30) Foreign Application Priority Data

Mar. 30, 2018 (JP) .................................. 2018-067067

(51) Int. Cl.
*A61M 16/00* (2006.01)
*A61M 16/08* (2006.01)
*A61M 16/10* (2006.01)

(52) U.S. Cl.
CPC .... *A61M 16/0066* (2013.01); *A61M 16/0875* (2013.01); *A61M 16/1045* (2013.01); *A61M 2209/084* (2013.01)

(58) Field of Classification Search
CPC .......... A61M 16/0066; A61M 16/0069; A61M 16/024; A61M 16/06; A61M 16/0816;
(Continued)

(56) References Cited

U.S. PATENT DOCUMENTS 10,668,236 B2 * 6/2020 O'Connor ........... A61M 16/026
11,247,007 B2 * 2/2022 Nitta ................... A61M 16/022
(Continued)

FOREIGN PATENT DOCUMENTS

| CN | 101296721 A | 10/2008 |
|---|---|---|
| JP | 2013-150684 A | 8/2013 |
| JP | 2016-034411 A | 3/2016 |

OTHER PUBLICATIONS

International Search Report for PCT/JP2019/012775 dated Jun. 11, 2019.
Written Opinion for PCT/JP2019/012775 dated Jun. 11, 2019.

*Primary Examiner* — Joshua Lee
(74) *Attorney, Agent, or Firm* — Pearne & Gordon LLP

(57) ABSTRACT

A continuous positive airway pressure (CPAP) apparatus includes: a first unit including a first housing provided with a first flow path that connects a first inlet port and a first outlet port and in which an air blower is provided; and a second unit including a second housing provided with a second flow path that connects a second inlet port and a second outlet port. The first flow path between the first inlet port and the air blower includes a first silencer. The second flow path includes a second silencer. In a first use state where the second unit is attached to the first unit, the second outlet port is connected to the first inlet port. In a second use state where the second unit is not attached to the first unit, the first inlet port is opened to the outside.

8 Claims, 14 Drawing Sheets

Related U.S. Application Data continuation of application No. PCT/JP2019/012775, filed on Mar. 26, 2019.

(58) Field of Classification Search
CPC .......... A61M 16/0875; A61M 16/1045; A61M 16/107; A61M 16/16; A61M 2016/0027; A61M 2016/0039; A61M 2205/123; A61M 2205/42; A61M 2205/505; A61M 2209/084

See application file for complete search history.

(56) References Cited

U.S. PATENT DOCUMENTS

| | | | | |
|---|---|---|---|---|
| 2001/0035186 A1* | 11/2001 | Hill | ...................... | A61M 16/00 128/204.23 |
| 2002/0005197 A1* | 1/2002 | DeVries | .............. | A61M 16/202 128/204.21 |
| 2006/0065270 A1* | 3/2006 | Li | ...................... | A61M 16/026 128/204.23 |
| 2007/0169776 A1 | 7/2007 | Kepler et al. | | |
| 2008/0251079 A1* | 10/2008 | Richey | .............. | A61M 16/0666 128/204.26 |
| 2008/0257346 A1 | 10/2008 | Lathrop et al. | | |
| 2012/0227738 A1* | 9/2012 | Virr | .................. | A61M 16/1095 128/204.21 |
| 2015/0165146 A1* | 6/2015 | Bowman | ............... | A61M 16/16 128/203.14 |
| 2015/0265787 A1* | 9/2015 | O'Connor | ............. | A61M 16/06 128/204.23 |
| 2015/0320954 A1* | 11/2015 | Suzuki | .................. | F04D 25/062 128/205.25 |
| 2016/0184539 A1* | 6/2016 | Suzuki | .................. | F04D 29/664 128/205.25 |
| 2017/0203064 A1* | 7/2017 | Suzuki | ............... | A61M 16/107 |
| 2017/0211438 A1 | 7/2017 | Suzuki et al. | | |
| 2018/0280643 A1* | 10/2018 | Nitta | ................... | A61M 16/022 |

* cited by examiner

CONTINUOUS POSITIVE AIRWAY PRESSURE APPARATUS

CROSS REFERENCE TO RELATED APPLICATION

This is a continuation of U.S. patent application Ser. No. 17/023,914 filed on Sep. 17, 2020, which is a continuation of International Application No. PCT/JP2019/012775 filed on Mar. 26, 2019, which claims priority from Japanese Patent Application No. 2018-067067 filed on Mar. 30, 2018. The contents of these applications are incorporated herein by reference in their entireties.

TECHNICAL FIELD

The present disclosure relates to a continuous positive airway pressure (CPAP) apparatus that feeds air, which is suctioned into the apparatus, to a user's respiratory tract for therapy of sleep apnea syndrome.

BACKGROUND ART

It is considered that sleep apnea syndrome causing interruption of breathing during sleep results from physically narrowing of a respiratory tract serving as an airway. One of effective therapeutic methods for sleep apnea syndrome is a method of therapy using a CPAP apparatus.

A CPAP apparatus serves to continuously feed air to a respiratory tract to open the respiratory tract in order to prevent apnea from occurring during sleep. More specifically, the CPAP apparatus includes an air blower for feeding air, which is suctioned into the apparatus, through an air tube to a mask put on a user's nose or mouth.

In this case, since the CPAP apparatus is used during bedtime and during sleep, this CPAP apparatus is required to operate quietly. The causes of disturbing quietness are an operating noise, a wind noise and the like from a drive motor that are generated mainly when the above-mentioned air blower operates. If leakage of these noises to the outside of the apparatus can be suppressed, the quietness can be improved.

Thus, for example, Japanese Patent Laying-Open No. 2016-34411 (PTL 1) discloses a CPAP apparatus configured such that a suction-side silencer is provided between an air inlet port provided in an apparatus main body equipped with an air blower and this air blower, and a discharge-side silencer is provided between an air outlet port provided in the apparatus main body and a mask.

BRIEF SUMMARY

In addition to the above-mentioned quietness, the CPAP apparatus is also strongly required to be reduced in size and weight. This is because the CPAP apparatus has to be used continuously every day, which requires a user to carry this CPAP apparatus, for example, when the user stays out overnight and the like.

Also, a silencer provided for improving the above-mentioned quietness is generally enhanced in silencing effect in proportion to its volume occupied in the apparatus. Accordingly, the so-called trade-off relation lies between quietness and reduction in a size and a weight of the apparatus. This significantly hinders the improvement in convenience of the CPAP apparatus.

Thus, the present disclosure has been made in light of the above-described problems, and one of the objects of the present disclosure is to provide a user-friendly CPAP apparatus that is excellent in portability and quietness.

A CPAP apparatus according to the present disclosure feeds air suctioned into the CPAP apparatus to a respiratory tract of a user. The CPAP apparatus includes a first unit and a second unit. The first unit includes an air blower and a first housing in which the air blower is housed. The second unit includes a second housing and is attachable to and detachable from the first unit. The first housing is provided with: a first inlet port through which air is introduced from outside the first housing; a first outlet port through which air is discharged from inside the first housing; and a first flow path in which the air blower is provided and that connects the first inlet port and the first outlet port. The second housing is provided with: a second inlet port through which air is introduced from outside the second housing; a second outlet port through which air is discharged from inside the second housing; and a second flow path that connects the second inlet port and the second outlet port. The first unit further includes a first silencer provided in a portion of the first flow path that is located between the first inlet port and the air blower. The second unit further includes a second silencer provided in the second flow path. In a first use state where the CPAP apparatus is used in a state where the second unit is attached to the first unit, the second outlet port is connected to the first inlet port. In a second use state where the CPAP apparatus is used in a state where the second unit is not attached to the first unit, the first inlet port is opened to outside.

In the CPAP apparatus according to the present disclosure, a volume occupying a portion functioning as the second silencer may be larger than a volume occupying a portion functioning as the first silencer.

In the CPAP apparatus according to the present disclosure, the first silencer may include a wide portion and a narrow portion that are disposed side by side in a direction in which the first flow path extends. Furthermore, in the CPAP apparatus according to the present disclosure, the second silencer may include a resonant tube that is branched from the second flow path.

In the CPAP apparatus according to the present disclosure, a cross-sectional area of the narrow portion that is orthogonal to an air flowing direction may be smaller than a cross-sectional area of the wide portion that is orthogonal to the air flowing direction, and the narrow portion may be disposed downstream from the wide portion in the air flowing direction.

In the CPAP apparatus according to the present disclosure, the first housing or the second housing may be provided with a gasket so as to surround each of the first inlet port and the second outlet port in the first use state.

In the CPAP apparatus according to the present disclosure, the second inlet port may be provided in a portion of the second housing that faces the first housing at a distance from the first housing in the first use state.

In the CPAP apparatus according to the present disclosure, the second inlet port is disposed at an outer surface of the second housing, and a concave portion is disposed at an outer surface of the first housing at a position facing the second inlet port, the concave portion being recessed from a surrounding area.

In an aspect of the CPAP apparatus according to the present disclosure, the second housing may be further provided with: a third inlet port through which air is introduced from outside the second housing; a third outlet port through which air is discharged from inside the second housing; and a third flow path that connects the third inlet port and the third outlet port. In this case, the second unit may further include a humidifying mechanism provided in the third flow path. In this case, it is preferable that the third inlet port is connected to the first outlet port in the first use state.

Furthermore, in the above-mentioned aspect, the first housing may include a mounting surface located vertically on a lower side in the first use state, and a first connection surface provided with the first inlet port and the first outlet port. The second housing may include a bottom plate portion disposed vertically on a lower side in the first use state. Furthermore, the second silencer and the humidifying mechanism may be disposed side by side in a horizontal direction on the bottom plate portion in the first use state. Also, the second housing may include: a stage surface located vertically above the second silencer in the first use state; an upper surface located vertically above the humidifying mechanism and located higher than the stage surface in the first use state; and a second connection surface connecting the stage surface and the upper surface and provided with the second outlet port and the third inlet port. Furthermore, in this case, the second unit may be attached to the first unit such that the mounting surface faces the stage surface and the first connection surface faces the second connection surface, so as to connect the second outlet port to the first inlet port and to connect the third inlet port to the first outlet port.

In another aspect of the CPAP apparatus according to the present disclosure, the apparatus may further include a third unit that includes a third housing and that is attachable to and detachable from the first unit. In this case, the third housing may be provided with: a third inlet port through which air is introduced from outside the third housing; a third outlet port through which air is discharged from inside the third housing; and a third flow path that connects the third inlet port and the third outlet port. In this case, the third unit may further include a humidifying mechanism provided in the third flow path. In this case, the third inlet port may be connected to the first outlet port in the first use state.

The present disclosure can provide a user-friendly CPAP apparatus that is excellent in portability and quietness.

DETAILED DESCRIPTION OF EMBODIMENTS

Figure 1:
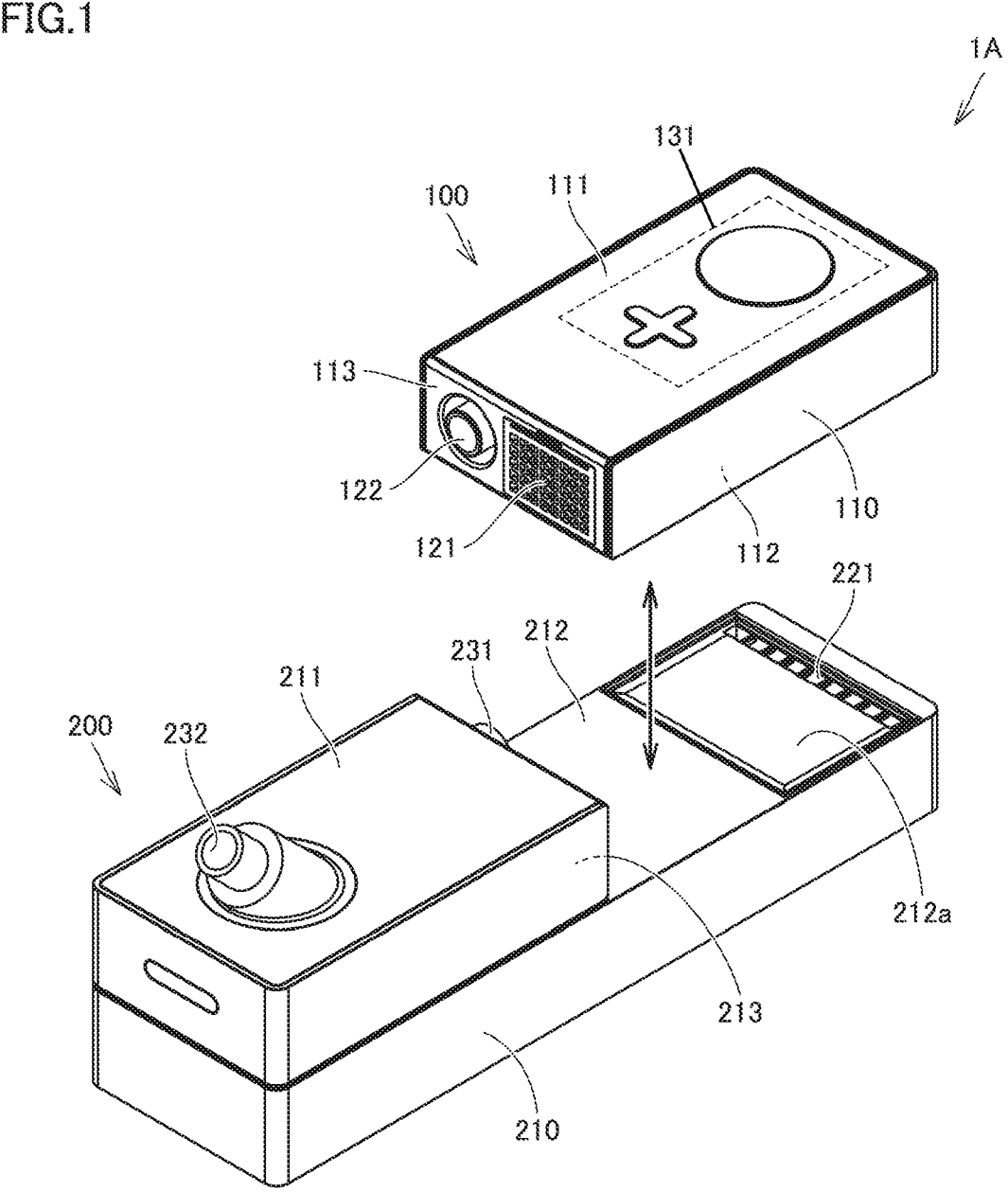
FIG. 1 is a perspective view showing the manner of attachment and detachment of a main body unit to/from a base unit of a CPAP apparatus according to the first embodiment.

In the following, embodiments of the present disclosure will be described in detail with reference to the accompanying drawings. In the embodiments described below, the same or common portions will be denoted by the same reference characters, and description thereof will not be repeated.

First Embodiment

Figure 2:
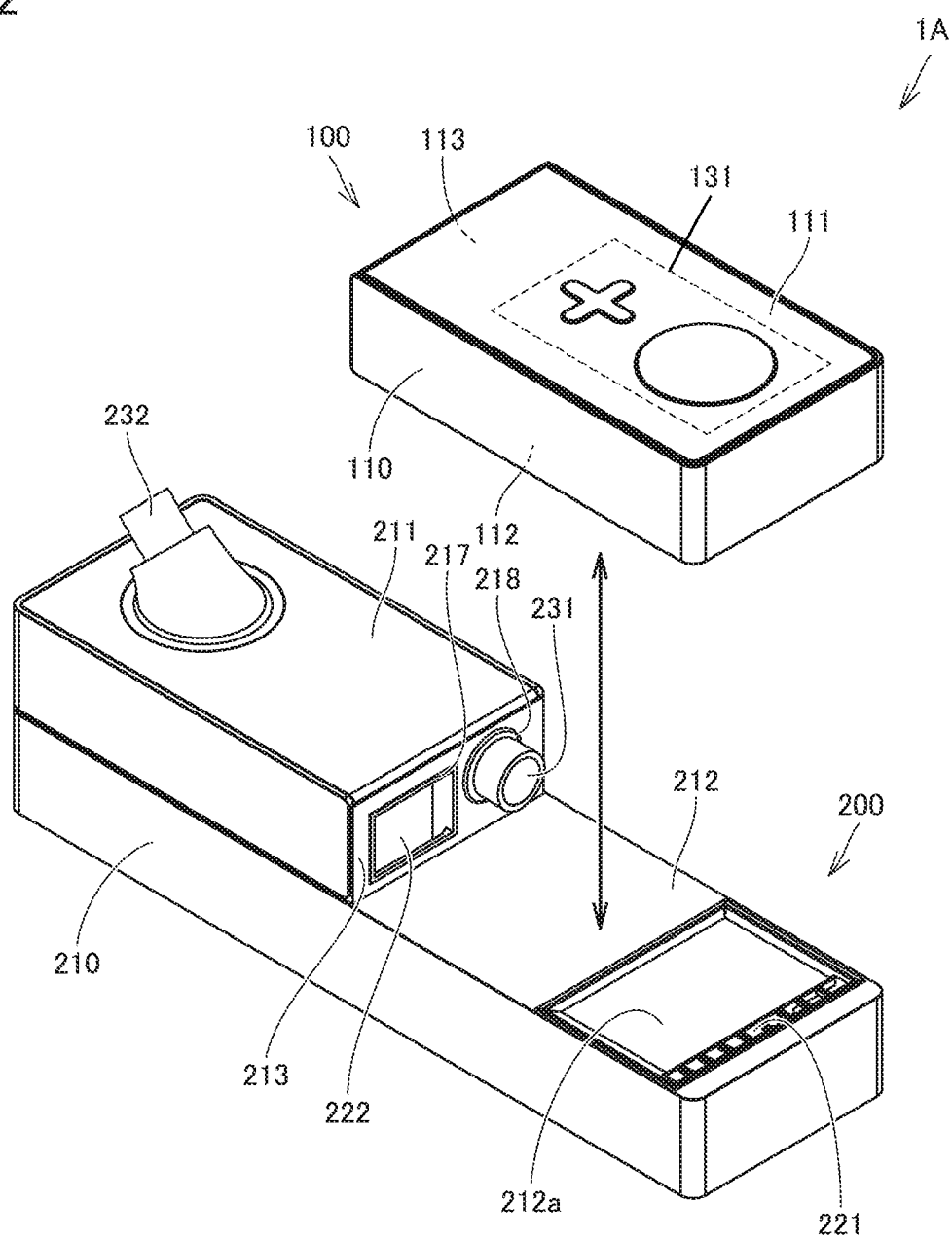
FIG. 2 is another perspective view of the manner of attachment and detachment shown in FIG. 1 as seen from a different angle.
Figure 3:
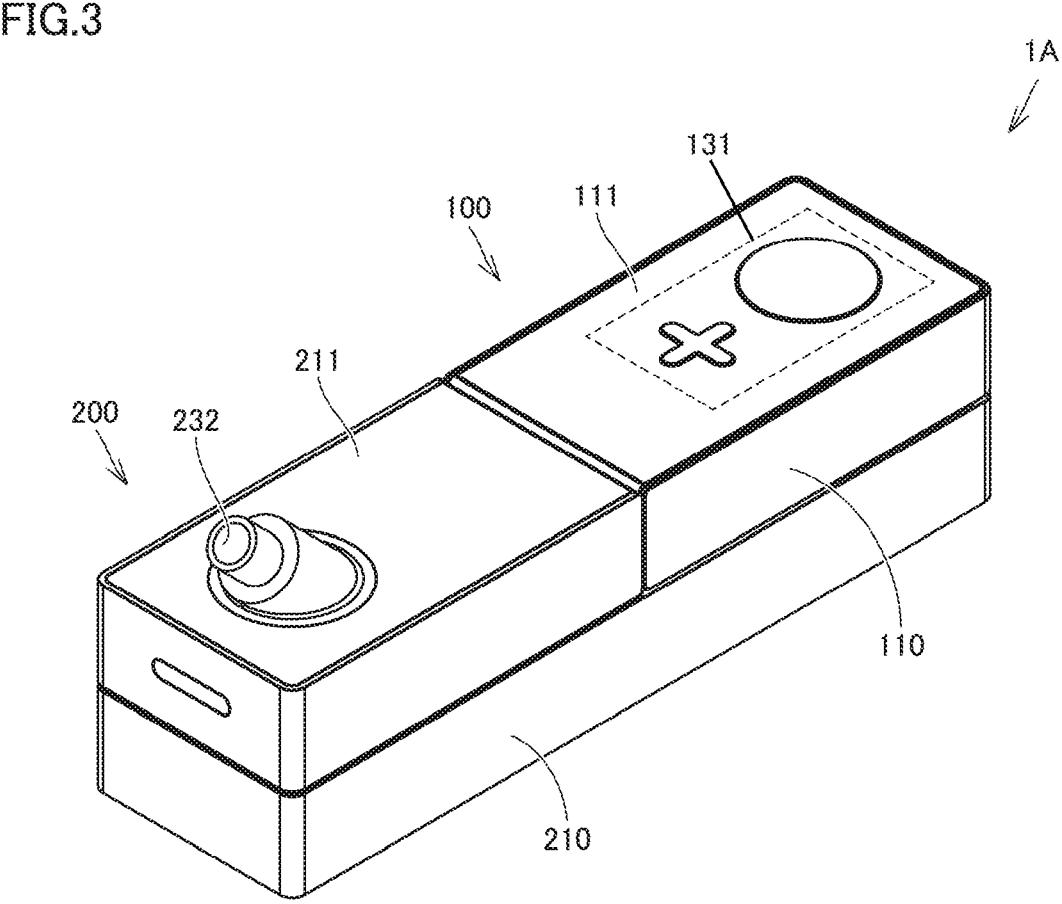
FIG. 3 is a perspective view showing the state where the main body unit is attached to the base unit in the CPAP apparatus according to the first embodiment.

FIG. 1 is a perspective view showing a manner of attachment and detachment of a main body unit to/from a base unit of a CPAP apparatus according to the first embodiment of the present disclosure. FIG. 2 is another perspective view of the manner of attachment and detachment shown in FIG. 1 as seen from a different angle. FIG. 3 is a perspective view showing the state where the main body unit is attached to the base unit in the CPAP apparatus according to the present embodiment. First, referring to FIGS. 1 to 3, an explanation will be given with regard to a schematic configuration of a CPAP apparatus 1A according to the present embodiment and the manner of attachment and detachment thereof.

As shown in FIGS. 1 to 3, CPAP apparatus 1A includes a main body unit 100 as the first unit, and a base unit 200 as the second unit. In this case, main body unit 100 mainly includes an air blower 140 and a first silencer 150 (see FIG. 5 to FIG. 9 and FIG. 12 and so on). Base unit 200 mainly includes a second silencer 240 and a humidifying mechanism 250 (see FIG. 5 and FIGS. 9 to 12 and so on).

Base unit 200 is attachable to and detachable from main body unit 100. In this case, CPAP apparatus 1A according to the present embodiment is configured to be usable in one of two states including the first use state where base unit 200 is attached to main body unit 100; and the second use state where base unit 200 is not attached to main body unit 100.

More specifically, in the first use state where CPAP apparatus 1A is used in the state where base unit 200 is attached to main body unit 100, both main body unit 100 and base unit 200 are used. In the second use state where CPAP apparatus 1A is used in the state where base unit 200 is not attached to main body unit 100, main body unit 100 is only used, and base unit 200 is not used.

This is because CPAP apparatus 1A has a configuration dividable into a plurality of units that are configured to be attachable to and detachable from one another so as to be highly convenient not only when a user stays at home but also when the user stays out overnight. In other words, during staying at home and the like, base unit 200 may be attached to main body unit 100, and thereby, CPAP apparatus 1A can be used in the above-mentioned first use state. During staying out overnight and the like, CPAP apparatus 1A can be used in the above-mentioned second use state without having to attach base unit 200 to main body unit 100.

Thus, although details will be described later, for example, during staying at home and the like, main body unit 100 having base unit 200 attached thereto is used to thereby allow excellent quietness. On the other hand, for example, during staying out overnight and the like, base unit 200 does not need to be carried but only main body unit 100 can be carried, thereby allowing excellent portability.

In this case, in CPAP apparatus 1A according to the present embodiment, a cutout portion that will be described later is provided at a prescribed position in base unit 200. Main body unit 100 is disposed so as to be fitted into this cutout portion, so that base unit 200 is attached to main body unit 100.

As shown in FIGS. 1 to 3, main body unit 100 has an approximately rectangular parallelepiped and flat outer shape, and has an outer casing formed of a first housing 110. First housing 110 has an upper surface and a lower surface that are arranged in the vertical direction in the use state, and four side surfaces that connect the upper surface and the lower surface.

The upper surface of first housing 110 forms an operation surface 111 on which an operation unit 131 is provided. The lower surface of first housing 110 forms a mounting surface 112 that is placed on base unit 200 in the first use state as described later and placed on a floor, a table and the like in the second use state as described later. Furthermore, one of the four side surfaces of first housing 110 forms a first connection surface 113 that is connected to base unit 200 in the first use state. First connection surface 113 is orthogonal to mounting surface 112.

As shown in FIGS. 1 to 3, base unit 200 has an approximately rectangular parallelepiped and elongated outer shape that has a portion provided with a cutout portion in the longitudinal direction, and has an outer casing formed of a second housing 210. Second housing 210 has an upper surface and a lower surface that are arranged in the vertical direction in the use state, and four side surfaces that connect the upper surface and the lower surface. The above-mentioned cutout portion is provided at a position on the upper surface side. Thereby, base unit 200 has a stepped shape formed such that a step is provided on its upper surface side at one end portion in the longitudinal direction.

The lower surface of second housing 210 forms a mounting surface that is to be placed on a floor, a table and the like in the first use state. A portion of the upper surface of second housing 210 that corresponds to the above-mentioned cutout portion forms a stage surface 212 on which main body unit 100 is placed in the first use state. Also, a remaining portion of the upper surface of second housing 210 forms a tube connection surface 211 that is provided with a third outlet port 232 to which an air tube 300 (see FIGS. 4A to 6 and the like) is connected in the first use state. In this case, tube connection surface 211 is to be located higher than stage surface 212 in the use state.

A portion included in the wall surface of second housing 210 that corresponds to the cutout portion and excluding stage surface 212 forms a second connection surface 213 that is connected to main body unit 100 in the first use state. Second connection surface 213 is orthogonal to stage surface 212 and located to connect stage surface 212 and tube connection surface 211.

As shown in FIG. 1, first connection surface 113 of first housing 110 is provided with a first inlet port 121 through which air is introduced from outside first housing 110, and a first outlet port 122 through which air is discharged from inside first housing 110.

Also, as shown in FIGS. 1 and 2, stage surface 212 of second housing 210 is provided with a second inlet port 221 through which air is introduced from outside second housing 210. As shown in FIG. 2, second connection surface 213 of second housing 210 is provided with a second outlet port 222 through which air is discharged from inside second housing 210.

Also, as shown in FIGS. 1 and 2, second connection surface 213 of second housing 210 is provided with a third inlet port 231 through which air is introduced from outside second housing 210. As shown in FIGS. 1 to 3, tube connection surface 211 of second housing 210 is provided with third outlet port 232 through which air is discharged from inside second housing 210.

Thus, in the state where main body unit 100 is disposed in the cutout portion provided in base unit 200 to thereby attach base unit 200 to main body unit 100, mounting surface 112 of first housing 110 is located to face stage surface 212 of second housing 210 while first connection surface 113 of first housing 110 is located to face second connection surface 213 of second housing 210. Accordingly, first inlet port 121 and first outlet port 122 that are provided in first connection surface 113 of first housing 110 are connected to second outlet port 222 and third inlet port 231, respectively, that are provided in second connection surface 213 of second housing 210. In this state where base unit 200 is attached to main body unit 100, CPAP apparatus 1A has an approximately rectangular parallelepiped outer shape as a whole. In other words, main body unit 100 has an outer shape that is approximately the same as the shape of the cutout portion.

On the other hand, in the state where base unit 200 is not attached to main body unit 100, first connection surface 113 of first housing 110 is exposed to the outside. Thus, each of first inlet port 121 and first outlet port 122 provided in first connection surface 113 of first housing 110 is opened to the outside.

Figure 4A:
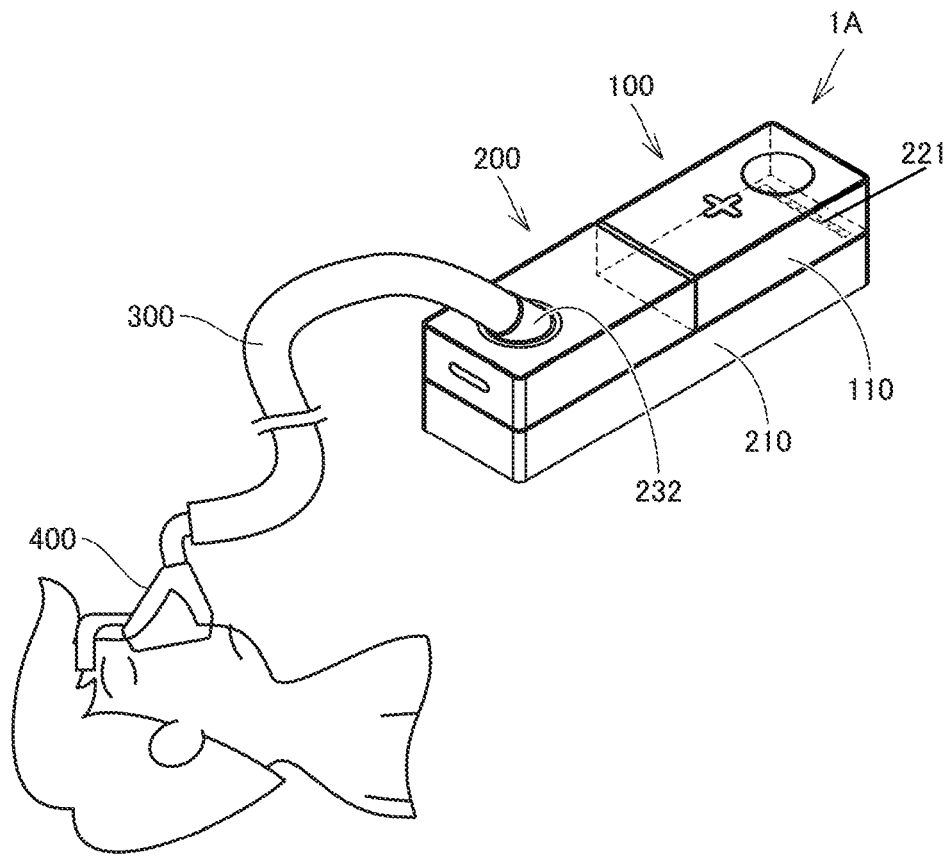
FIGS. 4A and 4B are diagrams schematically showing the first use state and the second use state of the CPAP apparatus according to the first embodiment.
Figure 4B:
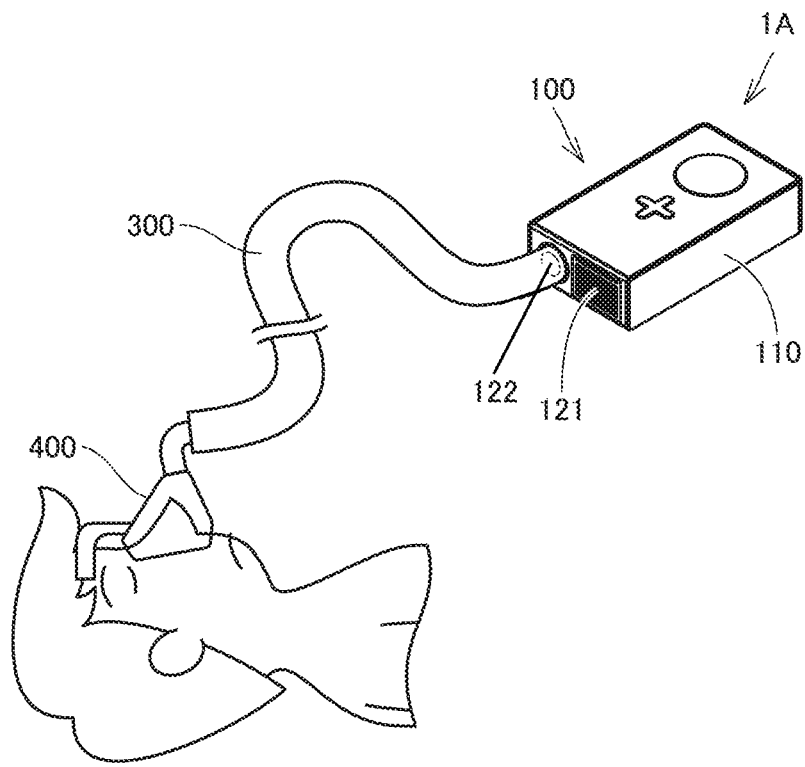

FIGS. 4A and 4B are diagrams schematically showing the use states of the CPAP apparatus according to the present embodiment. FIGS. 4A and 4B show the first use state and the second use state, respectively. The following are explanations about the first use state and the second use state of CPAP apparatus 1A according to the present embodiment with reference to this FIGS. 4A and 4B.

As shown in FIG. 4A, in the first use state, CPAP apparatus 1A is used in the state where base unit 200 is attached to main body unit 100, as described above. In this case, one end of air tube 300 is connected to third outlet port 232 provided in base unit 200 while a mask 400 is connected to the other end of air tube 300.

In the first use state, air blower 140 provided in main body unit 100 is driven, and thereby, air is suctioned into CPAP apparatus 1A from second inlet port 221 provided in base unit 200, and then, the suctioned air is discharged from third outlet port 232 provided in base unit 200 to the outside of CPAP apparatus 1A. Thereby, the air discharged from third outlet port 232 is to be fed through air tube 300 and mask 400 into a user's respiratory tract.

As shown in FIG. 4B, in the second use state, CPAP apparatus 1A is used in the state where base unit 200 is not attached to main body unit 100, as described above. In this case, one end of air tube 300 is connected to first outlet port 122 provided in main body unit 100 while mask 400 is connected to the other end of air tube 300.

In the second use state, air blower 140 provided in main body unit 100 is driven, and thereby, air is suctioned into CPAP apparatus 1A from first inlet port 121 provided in main body unit 100, and then, the suctioned air is discharged from first outlet port 122 provided in main body unit 100 to the outside of CPAP apparatus 1A. Thereby, the air discharged from first outlet port 122 is to be fed through air tube 300 and mask 400 into the user's respiratory tract.

In this case, mask 400 is attached to the user so as to cover the user's nose or mouth, for example. Mask 400 having a suitable shape and structure for the user can be selected from among various types of masks, and the shape and the structure shown in FIGS. 4A and 4B are merely by way of example.

In addition, CPAP apparatus 1A serves to continuously feed air to the user's respiratory tract to open the respiratory tract while adjusting the timing of feeding air to the timing of the user's breathing in order to prevent apnea from occurring during sleep. Accordingly, in CPAP apparatus 1A, in each of the first use state and the second use state, a control unit 130 performs various types of control such as feedback control and feedforward control, for example, based on the flow rate value, the pressure value and the like that are detected by a flow rate sensor 132 and a pressure sensor 133. Thereby, the rotation speed of air blower 140 is increased or decreased to adjust the air feeding amount and the like, so as to prevent apnea from occurring while the user is sleeping.

Figure 5:
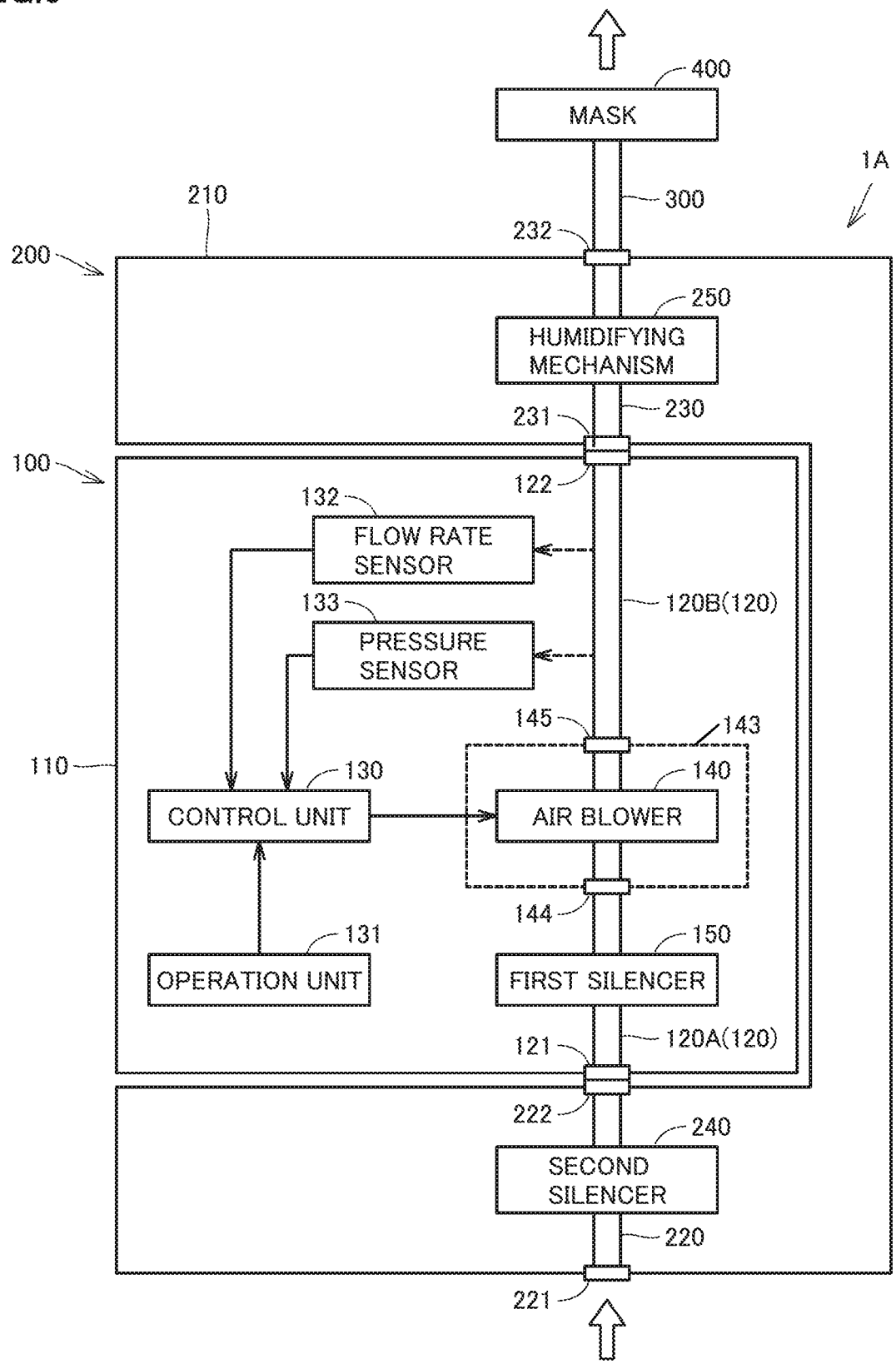
FIG. 5 is a diagram showing a functional block configuration in the first use state of the CPAP apparatus according to the first embodiment.
Figure 6:
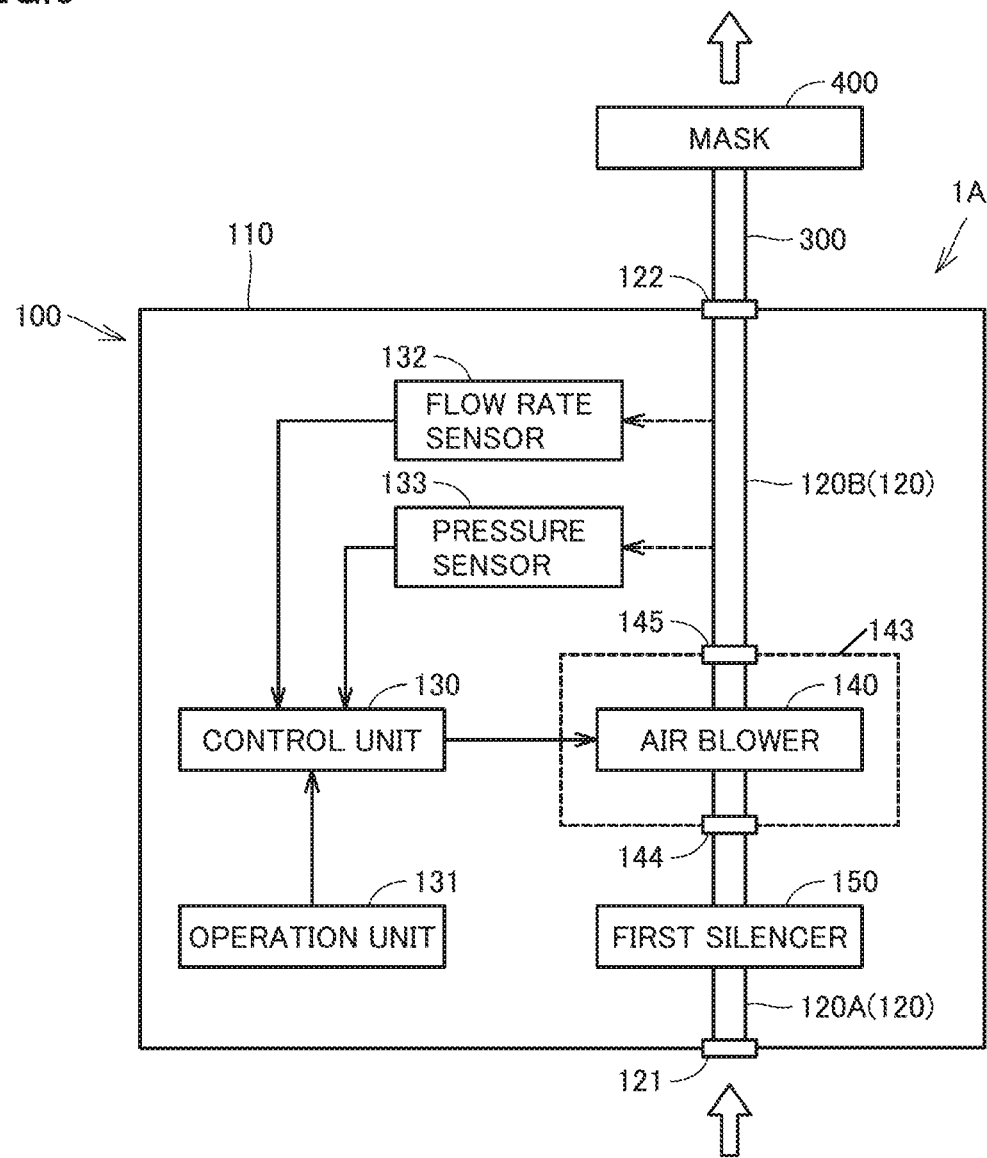
FIG. 6 is a diagram showing a functional block configuration in the second use state of the CPAP apparatus according to the first embodiment.

FIG. 5 is a diagram showing a functional block configuration in the first use state of the CPAP apparatus according to the present embodiment. FIG. 6 is a diagram showing a functional block configuration in the second use state of the CPAP apparatus. Then, referring to FIGS. 5 and 6, the functional block configuration of CPAP apparatus 1A according to the present embodiment will be hereinafter described.

As shown in FIGS. 5 and 6, CPAP apparatus 1A includes control unit 130, operation unit 131, flow rate sensor 132, pressure sensor 133, air blower 140, first silencer 150, second silencer 240, and humidifying mechanism 250. Specifically, control unit 130, operation unit 131, flow rate sensor 132, pressure sensor 133, air blower 140, and first silencer 150 are provided in main body unit 100 while second silencer 240 and humidifying mechanism 250 are provided in base unit 200.

As shown in FIGS. 5 and 6, first housing 110 of main body unit 100 is provided with a first flow path 120 in addition to first inlet port 121 and first outlet port 122 as mentioned above. First flow path 120 is configured to connect first inlet port 121 and first outlet port 122.

Air blower 140 is provided in first flow path 120. Air blower 140 is formed of a centrifugal fan, for example. Air blower 140 is installed in an air blower chamber 117, as described later in association with FIGS. 7 to 9 and FIG. 12, provided in first housing 110, and thus, disposed on first flow path 120.

In this case, air blower 140 has a casing 143 that is provided with an intake port 144 and a discharge port 145 of air blower 140. Thus, first flow path 120 includes an upstream-side flow path portion 120A that connects first inlet port 121 provided in first housing 110 and intake port 144 provided in air blower 140, and a downstream-side flow path portion 120B that connects discharge port 145 provided in air blower 140 and first outlet port 122 provided in first housing 110.

First silencer 150 is provided in upstream-side flow path portion 120A located between first inlet port 121 and intake port 144 in first flow path 120. First silencer 150 serves to suppress leakage of a noise occurring in air blower 140 (an operation noise, a wind noise and the like from a drive motor 142 as described later in association with FIGS. 7 to 9 and FIG. 12, provided in air blower 140) to the outside through first inlet port 121 in each of the first use state and the second use state.

As shown in FIG. 5, second housing 210 of base unit 200 is provided with a second flow path 220 and a third flow path 230 in addition to second inlet port 221, second outlet port 222, third inlet port 231, and third outlet port 232 as mentioned above. Second flow path 220 is configured to connect second inlet port 221 and second outlet port 222. Third flow path 230 is configured to connect third inlet port 231 and third outlet port 232.

Second silencer 240 is provided in second flow path 220. Second silencer 240 serves to suppress leakage of the above-mentioned noise occurring in air blower 140 to the outside through second inlet port 221 in the first use state.

Humidifying mechanism 250 is provided in third flow path 230. Humidifying mechanism 250 serves to apply appropriate moisture to the air that is to be fed toward the user's respiratory tract in the first use state. Examples of applicable humidifying mechanism 250 may be various types of known humidifying devices such as a heating-type humidifying device, an ultrasonic-type humidifying device, and an evaporation-type humidifying device. A heating-type humidifying device can be applied in the present embodiment. The humidifying mechanism is not indispensable, and may not be provided as a matter of course.

Control unit 130 includes, as main components, a central processing unit (CPU) that executes a program, a read only memory (ROM)/random access memory (RAM), a drive unit that drives air blower 140, and the like. The ROM/RAM includes a ROM in which data is stored in a non-volatile manner, and a RAM in which data generated by the CPU executing the program and data input through operation unit 131 are stored in a volatile manner. The components of control unit 130 are connected to one another by a data bus.

The process in the CPU is implemented by each hardware and software executed by the CPU. Such software is stored in the ROM/RAM in advance. Software also implements reception of the operation through operation unit 131, control of drive motor 142 to drive air blower 140, and the like.

Control unit 130 is supplied with electric power by an internal power supply (not shown) or an external power supply (not shown), and connected to the external power supply, for example, through an alternating-current (AC) adapter (not shown) and the like. Similar to control unit 130, flow rate sensor 132 and pressure sensor 133 each are also supplied with electric power by an internal power supply (not shown) or an external power supply (not shown). Flow rate sensor 132 serves to measure the flow rate of air between CPAP apparatus 1A and air tube 300. Pressure sensor 133 serves to measure the pressure of air that is supplied from air blower 140. Control unit 130 performs various controls, such as feedback control and feedforward control, for example, based on the flow rate value, the pressure value and the like that are detected by flow rate sensor 132 and pressure sensor 133, thereby increasing or decreasing the rotation speed of air blower 140. In the case where the above-mentioned internal power supply is provided, the internal power supply is provided only in main body unit 100.

CPAP apparatus 1A may also be separately provided with a display unit including a liquid crystal display (LCD), an organic electro-luminescence (EL) display, or the like. In this case, the display unit may be provided in main body unit 100 or may be provided in base unit 200. Furthermore, operation unit 131 does not necessarily need to be a button having a physical shape as shown in the figure, but may be a touch panel or the like provided on the display surface of the LCD, for example. Buttons on operation unit 131 other than the button for switching the power supply to be turned ON/OFF may be provided in base unit 200. Such a configuration allows main body unit 100 to be further reduced in size and weight.

In this case, as shown in FIG. 5, in the first use state, first inlet port 121 provided in first housing 110 is connected to second outlet port 222 provided in second housing 210 while first outlet port 122 provided in first housing 110 is connected to third inlet port 231 provided in second housing 210. Thereby, in the first use state, second flow path 220 is connected to the upstream side of first flow path 120 while third flow path 230 is connected to the downstream side of first flow path 120.

Accordingly, in the first use state, air blower 140 is driven to thereby cause the air suctioned from second inlet port 221 to flow through second flow path 220, first flow path 120 and third flow path 230 sequentially in this order so as to be discharged from third outlet port 232. The air discharged from third outlet port 232 is then fed through air tube 300 and mask 400 into the user's respiratory tract. In other words, in the first use state, second inlet port 221 functions as an air intake port through which air is suctioned into CPAP apparatus 1A, and third outlet port 232 functions as an exhaust port through which air is discharged from inside CPAP apparatus 1A.

On the other hand, as shown in FIG. 6, in the second use state, first inlet port 121 provided in first housing 110 is opened to the outside.

Thus, in the second use state, air blower 140 is driven to thereby cause the air suctioned from first inlet port 121 to be discharged from first outlet port 122 through first flow path 120. The air discharged from first outlet port 122 is then fed through air tube 300 and mask 400 into the user's respiratory tract. In other words, in the second use state, first inlet port 121 functions as an air intake port through which air is suctioned into CPAP apparatus 1A while first outlet port 122 functions as an exhaust port through which air is discharged from inside CPAP apparatus 1A.

Accordingly, in the first use state, CPAP apparatus 1A is provided with second silencer 240 as compared with the second use state. Thus, not only first silencer 150 but also second silencer 240 can function to suppress leakage of the noise in air blower 140 through the air intake port of CPAP apparatus 1A to the outside.

Furthermore, in the first use state, CPAP apparatus 1A is provided with humidifying mechanism 250 as compared with the second use state. Thus, appropriate moisture can be applied to the air that is to be fed to the user's respiratory tract.

On the other hand, in the second use state, CPAP apparatus 1A is not provided with second silencer 240 and humidifying mechanism 250 as compared with the first use state. Thus, CPAP apparatus 1A can be entirely reduced in size and weight, thereby allowing excellent portability.

In this way, first silencer 150 and second silencer 240 are located upstream from air blower 140 in the air flowing direction, so that leakage of noise from first inlet port 121 or second inlet port 221 can be reduced. Furthermore, as humidifying mechanism 250 is located downstream from air blower 140 in the air flowing direction in this way, highly humid air can be prevented from passing through air blower 140, and thereby, various electronic components including air blower 140 can be prevented beforehand from being damaged by moisture.

Figure 7:
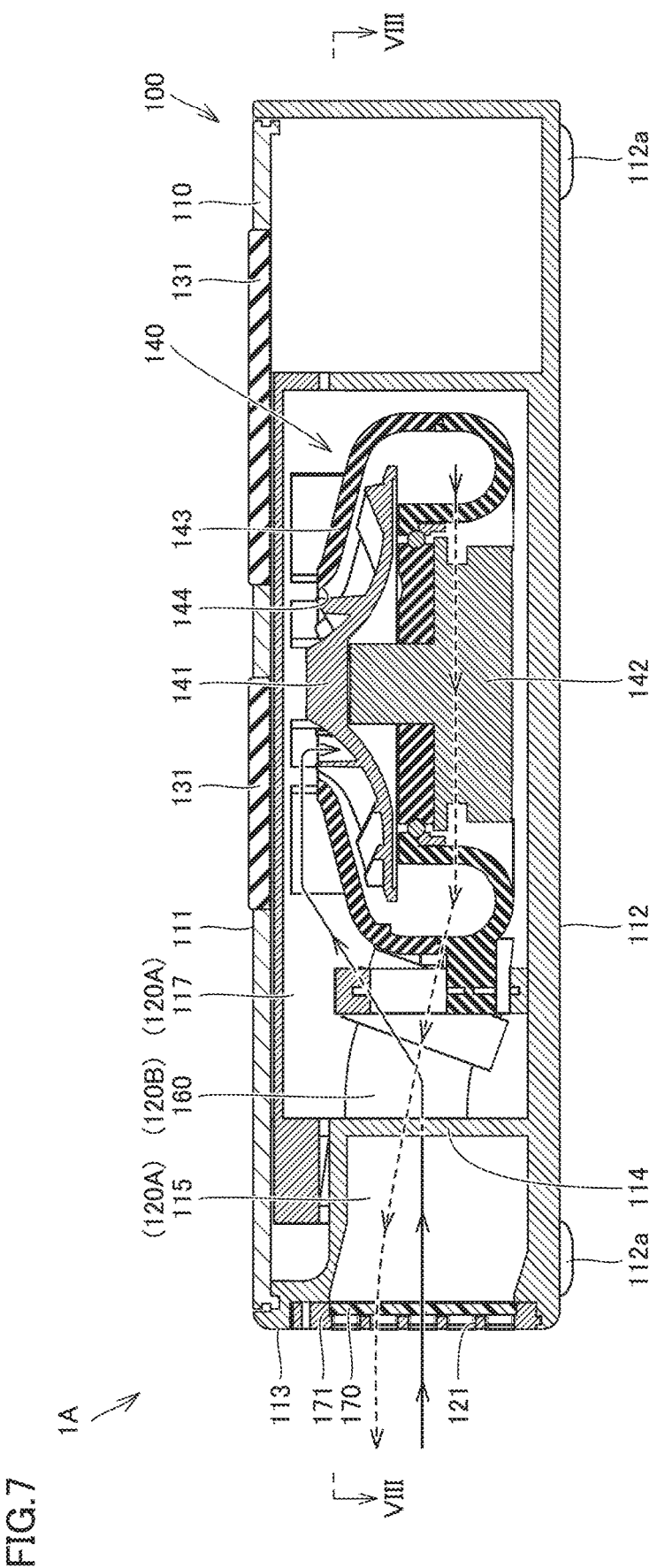
FIG. 7 is a schematic cross-sectional view in the second use state of the CPAP apparatus according to the first embodiment.
Figure 8:
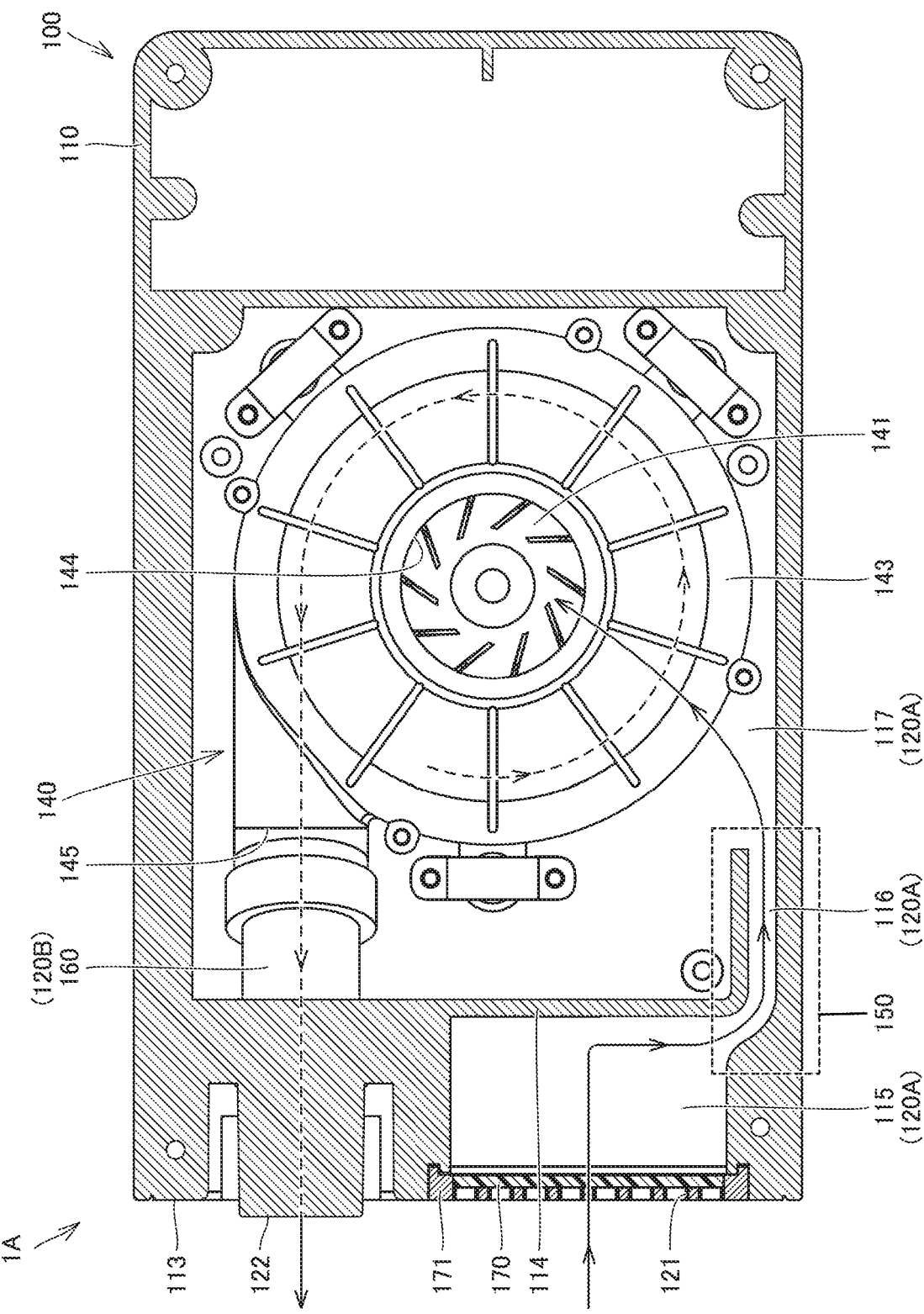
FIG. 8 is a schematic cross-sectional view taken along a line VIII-VIII shown in FIG. 7.

FIG. 7 is a schematic cross-sectional view in the second use state of the CPAP apparatus according to the present embodiment. FIG. 8 is a schematic cross-sectional view taken along a line VIII-VIII shown in FIG. 7. The following is an explanation with reference to FIG. 7 and FIG. 8 about the detailed structure of main body unit 100 in CPAP apparatus 1A according to the present embodiment and the flow of air inside CPAP apparatus 1A in the second use state. In each of FIGS. 7 and 8, the flow of air generated by the operation of air blower 140 is schematically shown by arrows.

As shown in FIGS. 7 and 8, the space inside first housing 110 of main body unit 100 is provided with various types of walls, hoses and the like, and thereby partitioned into a plurality of chambers. The plurality of chambers include a wide portion 115, a narrow portion 116, and air blower chamber 117. Such wide portion 115, narrow portion 116, and air blower chamber 117 correspond to upstream-side flow path portion 120A as mentioned above.

Wide portion 115 is disposed adjacent to first inlet port 121 provided in first connection surface 113 of first housing 110. The cross-sectional area of wide portion 115 that is orthogonal to the air flowing direction (i.e., the area of the cross section of wide portion 115 that is taken along a line in parallel to the opening plane of first inlet port 121) is formed relatively large so as to reduce the pressure loss that may occur in first inlet port 121. In addition, the cross-sectional area of wide portion 115 that is orthogonal to the air flowing direction is formed larger than the cross-sectional area of narrow portion 116 that is orthogonal to the air flowing direction.

In this case, first inlet port 121 is provided with a filter 170 through which foreign substances such as dust contained in air are captured. In order to fix filter 170 to first connection surface 113, first connection surface 113 is equipped with a filter cover 171 that forms a part of first housing 110. Filter cover 171 is provided with a plurality of holes arranged in rows and columns. The plurality of holes form first inlet port 121.

Narrow portion 116 is disposed adjacent to wide portion 115. This narrow portion 116 is formed by providing a separation wall portion 114 inside first housing 110 and configured to have a relatively small cross-sectional area that is orthogonal to the air flowing direction (the area of the cross section of narrow portion 116 that is taken along a line in parallel to the opening plane of first inlet port 121). The cross-sectional area of narrow portion 116 that is orthogonal to the air flowing direction is smaller than the cross-sectional area of the above-mentioned wide portion 115 that is orthogonal to the air flowing direction.

Air blower chamber 117 is disposed adjacent to narrow portion 116. Air blower 140 is housed inside air blower chamber 117. This air blower chamber 117 is configured to have a relatively large cross-sectional area that is orthogonal to the air flowing direction (i.e., the area of the cross section of air blower chamber 117 that is taken along a line in parallel to the opening plane of first inlet port 121). Air blower chamber 117 has a relatively large space that occupies most of first housing 110. The cross-sectional area of air blower chamber 117 that is orthogonal to the air flowing direction is larger than the cross-sectional area of narrow portion 116 that is orthogonal to the air flowing direction.

In this case, first flow path 120 corresponding to wide portion 115 and narrow portion 116 is a section formed such that its cross-sectional area orthogonal to the air flowing direction is abruptly increased from downstream to upstream in the air flowing direction. This section is to function as first silencer 150 as mentioned above.

In other words, first silencer 150 is formed of a so-called muffler-type silencer including wide portion 115 and narrow portion 116 that are arranged side by side in the direction in which first flow path 120 extends. The cross-sectional area of narrow portion 116 that is orthogonal to the air flowing direction is smaller than the cross-sectional area of wide portion 115 that is orthogonal to the air flowing direction as described above. Also, narrow portion 116 is disposed downstream from wide portion 115 in the air flowing direction. By the configuration as described above, the noise occurring in air blower 140 is attenuated as a result of irregular reflection or the like of this noise passing through first silencer 150, with the result that leakage of the noise through first inlet port 121 can be suppressed.

In addition, the cross-sectional area of narrow portion 116 that is orthogonal to the air flowing direction is suitably equal to or less than the half of the cross-sectional area of wide portion 115 that is orthogonal to the air flowing direction. This configuration can effectively suppress leakage of the noise through first inlet port 121.

First silencer 150 having the above-mentioned configuration is effective at reducing the noise in a relatively high frequency band of about 1500 Hz or more, but cannot necessarily sufficiently reduce the noise in the frequency band lower than this relatively high frequency band. However, first silencer 150 having the above-mentioned configuration can be reduced in volume occupied inside first housing 110, and therefore, contribute to downsizing of main body unit 100.

Therefore, when not only reduction of the noise in a relatively high frequency band is required, but also when reduction of the noise in a lower frequency band is particularly required, for example, a sound-absorbing member is further attached to the inner wall surface of first housing 110 that forms upstream-side flow path portion 120A, thereby allowing reduction of the noise in a wider frequency band while allowing downsizing of main body unit 100.

Air blower 140 is formed of a centrifugal fan, for example, and fixed to a wall portion that defines mounting surface 112 of first housing 110 (i.e., a bottom plate portion) in the state where air blower 140 is housed in air blower chamber 117. Air blower 140 includes an impeller 141, a drive motor 142, and a casing 143.

Impeller 141 is fixed to the rotation shaft of drive motor 142. Thus, drive motor 142 is driven to thereby rotate impeller 141. Impeller 141 is rotated to stir air to thereby apply centrifugal force to air, which generates an airflow inside casing 143, with the result that air is suctioned from intake port 144 provided in casing 143, and discharged from discharge port 145 provided in casing 143.

Intake port 144 of air blower 140 is provided in a portion of casing 143 that is located above the shaft portion of impeller 141, and disposed to face the inner surface of the wall portion (i.e., a top plate portion) that defines operation surface 111 of first housing 110 at a distance from this inner surface. On the other hand, in a view seen along the shaft portion of impeller 141, discharge port 145 of air blower 140 is provided in a portion of casing 143 that is tangent to the outer edge of impeller 141, and disposed at a prescribed distance from impeller 141.

In this case, intake port 144 of air blower 140 is in communication with air blower chamber 117. Also, discharge port 145 of air blower 140 is disposed to cross air blower chamber 117 and has one end connected to the other end of hose 160 connected to first outlet port 122 provided in first housing 110. The space inside hose 160 corresponds to downstream-side flow path portion 120B as mentioned above.

First connection surface 113 of first housing 110 is provided with first outlet port 122. First outlet port 122 has a nozzle shape so as to allow air tube 300 connected thereto.

Thus, in the second use state, as described above, the air suctioned from first inlet port 121 is discharged from first outlet port 122 through first flow path 120. More specifically, the air suctioned from first inlet port 121 flows sequentially through wide portion 115, narrow portion 116, air blower chamber 117, air blower 140, and hose 160 provided in first housing 110, and then, is discharged from first outlet port 122.

Figure 9:
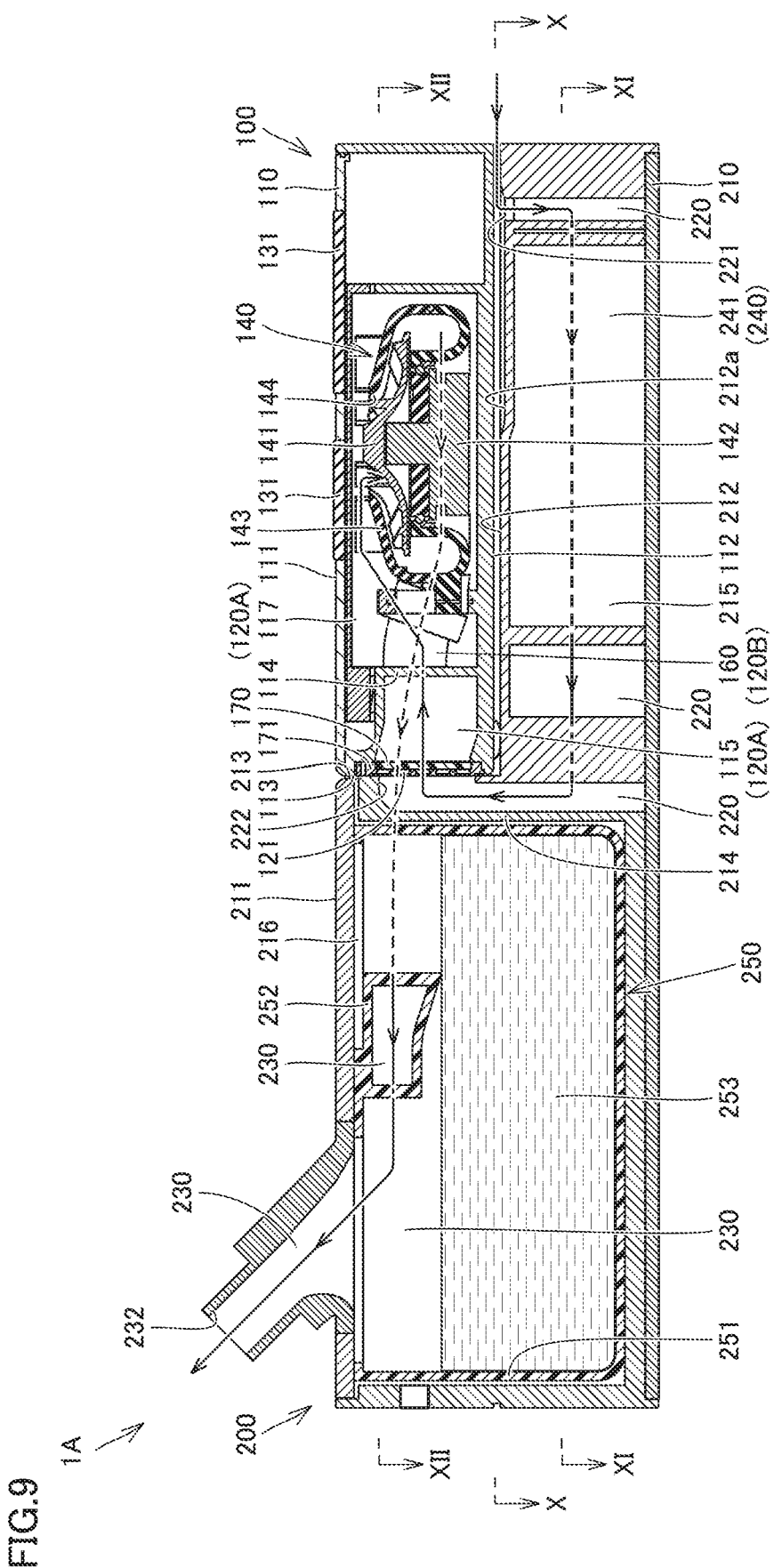
FIG. 9 is a schematic cross-sectional view in the first use state of the CPAP apparatus according to the first embodiment.
Figure 10:
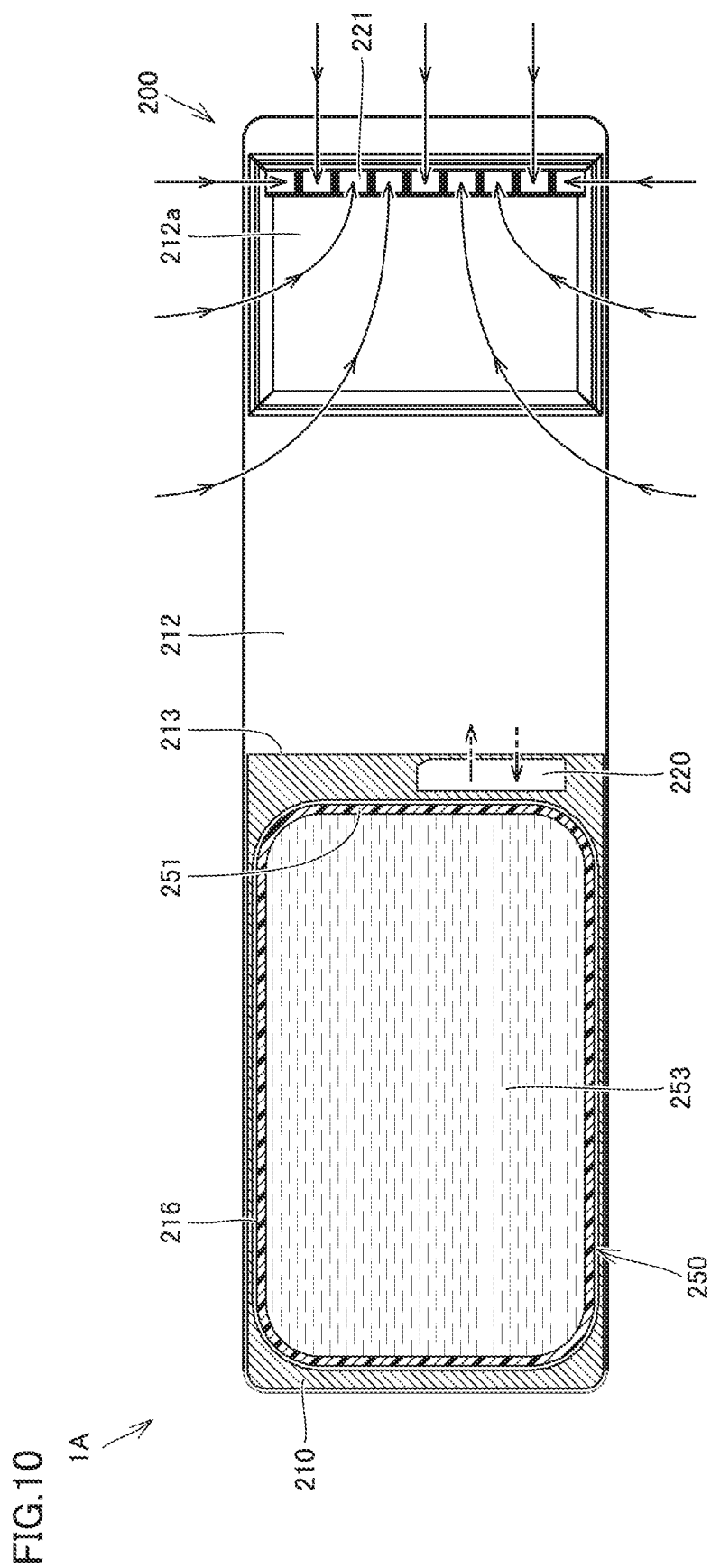
FIG. 10 is a schematic cross-sectional view taken along a line X-X shown in FIG. 9.
Figure 11:
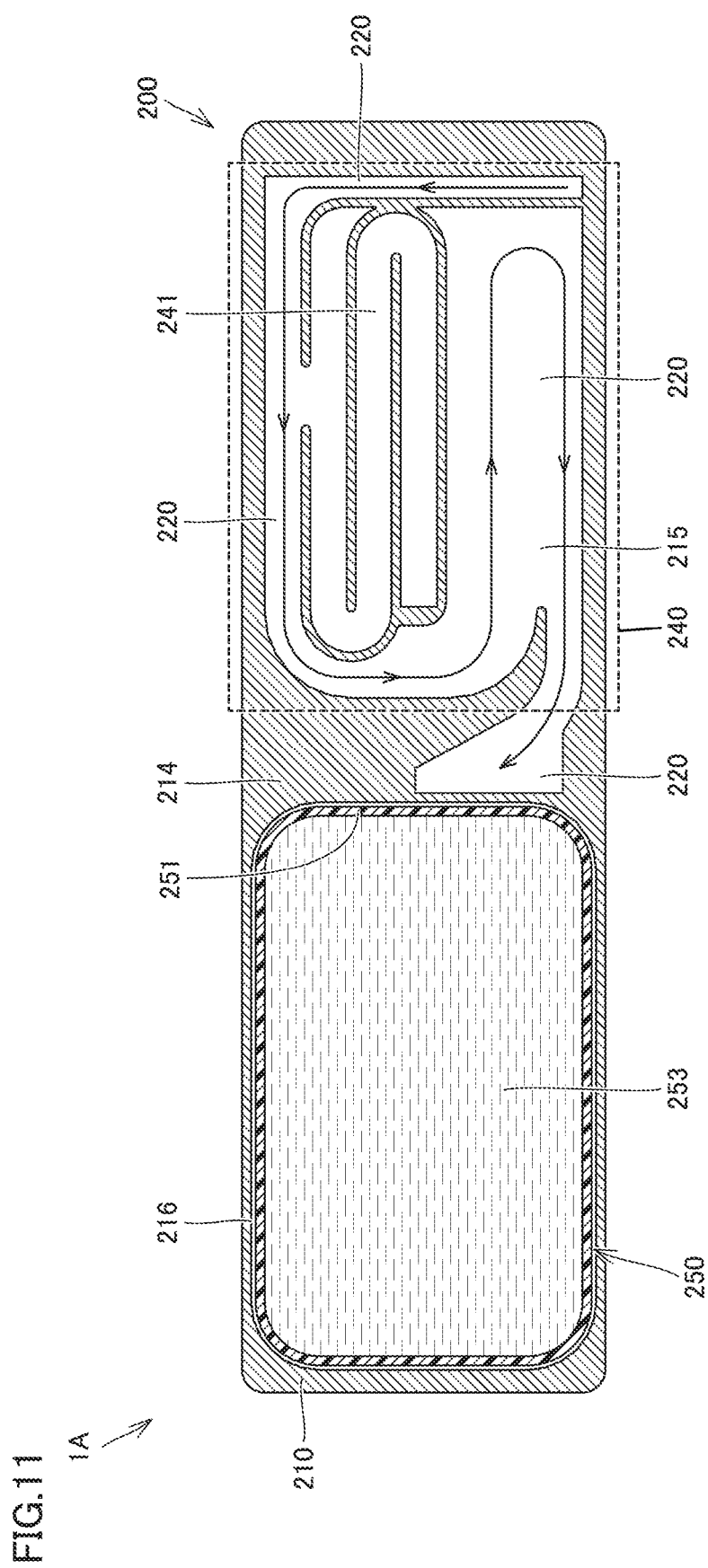
FIG. 11 is a schematic cross-sectional view taken along a line XI-XI shown in FIG. 9.
Figure 12:
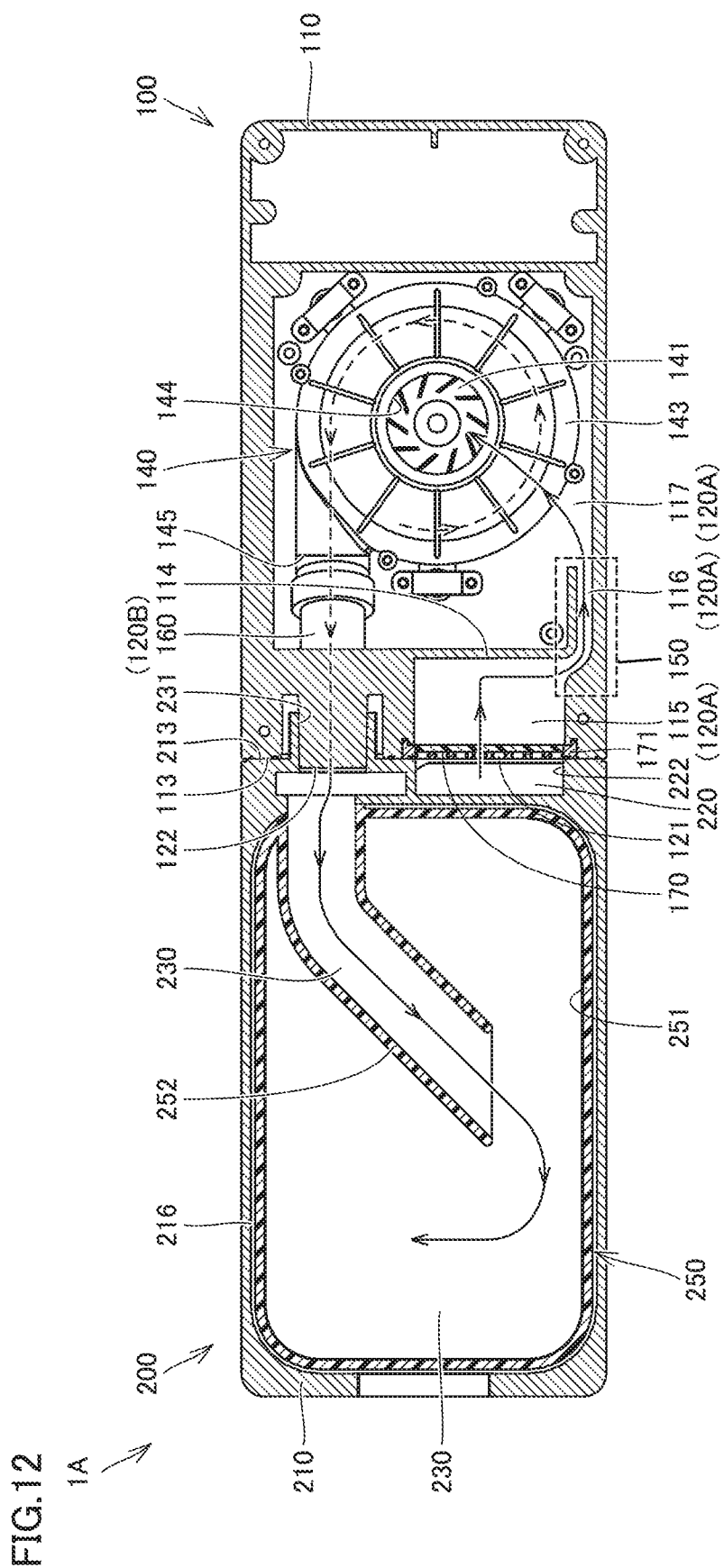
FIG. 12 is a schematic cross-sectional view taken along a line XII-XII shown in FIG. 9.

FIG. 9 is a schematic cross-sectional view in the first use state of the CPAP apparatus according to the present embodiment. FIGS. 10, 11 and 12 are schematic cross-sectional views taken along a line X-X, a line XI-XI and a line XII-XII, respectively, shown in FIG. 9. The following is an explanation with reference to FIGS. 9 and 12 about the detailed structure of base unit 200 in CPAP apparatus 1A according to the present embodiment and the flow of air inside CPAP apparatus 1A in the first use state. In each of FIGS. 9 to 12, the flow of air generated by the operation of air blower 140 is schematically shown by arrows.

As shown in FIGS. 9 to 12, the space inside second housing 210 of base unit 200 is partitioned into a first chamber 215 and a second chamber 216 by a partition wall 214 provided in an approximately center portion of second housing 210 in the longitudinal direction. First chamber 215 is provided as a space in the portion adjacent to main body unit 100 (i.e., a space in the portion adjacent to main body unit 100 among a space below main body unit 100 and a space located on the lateral side of main body unit 100) in the state where base unit 200 is attached to main body unit 100. Second chamber 216 is provided as a remaining space.

As shown in FIGS. 9 and 11, a wall portion having a prescribed shape is provided in the space inside first chamber 215, thereby providing second flow path 220 and second silencer 240. Second flow path 220 is provided so as to connect second inlet port 221 provided in stage surface 212 of second housing 210 to second outlet port 222 provided in second connection surface 213 of second housing 210. Second silencer 240 is formed of a resonant tube 241 that is branched from second flow path 220.

Second flow path 220 extends along the circumferential wall of the portion that defines first chamber 215 of second housing 210. Resonant tube 241 is disposed near the center portion of first chamber 215 so as to be surrounded by second flow path 220. Resonant tube 241 is formed of a flow path having a meandering shape.

This resonant tube 241 is also called a Helmholtz resonator or a resonator, and has a function to attenuate the noise in a prescribed frequency band. In this case, the frequency band of the noise attenuated by resonant tube 241 depends on the natural frequency of resonant tube 241. Accordingly, for example, the length and the like of resonant tube 241 are adjusted as appropriate, to thereby particularly allow reduction of the noise in a frequency band lower than about 1500

Hz (for example, around 400 Hz) that cannot be sufficiently reduced by the above-mentioned first silencer 150.

Second silencer 240 having the above-mentioned configuration is effective at reducing the noise in a specific frequency band as described above, and therefore, cannot necessarily sufficiently reduce the noise in a frequency band other than the above-mentioned frequency band. Accordingly, in the case where the noise in a wider frequency band particularly needs to be reduced, for example, a sound-absorbing member may be further attached to the inner wall surface of second housing 210 that forms second flow path 220.

In this case, as shown in FIG. 9, in the state where base unit 200 is attached to main body unit 100, mounting surface 112 of first housing 110 and stage surface 212 of second housing 210 are disposed at a prescribed distance (for example, about 1.5 mm) from each other. More specifically, referring to FIG. 7, four corners of mounting surface 112 of first housing 110 are provided with legs 112a protruding downward. Legs 112a come into contact with stage surface 212 of second housing 210, thereby implementing the above-mentioned configuration.

Thereby, second inlet port 221 provided in stage surface 212 of base unit 200 is located to face first housing 110 at a distance from first housing 110, and second inlet port 221 is not blocked by first housing 110. Furthermore, second inlet port 221 is in communication with the space outside CPAP apparatus 1A through the gap formed between first housing 110 and second housing 210.

Therefore, by the configuration as described above, air is suctioned from every direction toward stage surface 212 in the portion provided with second inlet port 221, as shown in FIG. 10, thereby allowing efficient suction of air. Also, first housing 110 is located to face second inlet port 221, thereby allowing effective suppression of leakage of the noise through second inlet port 221 to the outside.

Furthermore, as shown in FIGS. 9 and 10 and FIGS. 1 and 2 mentioned above, stage surface 212 of second housing 210 is provided with a concave portion 212a that is recessed from other portions of stage surface 212. Concave portion 212a is provided with second inlet port 221. In other words, a portion of the outer surface of second housing 210 that includes the position provided with second inlet port 221 (i.e., a part of stage surface 212) is formed as concave portion 212a that is recessed from the surrounding area.

By the configuration as described above, concave portion 212a and the portion that is located close to second inlet port 221 of second flow path 220 and that is in communication with concave portion 212a are formed as a section in which its cross-sectional area orthogonal to the air flowing direction is abruptly increased from downstream to upstream in the air flowing direction.

In other words, second inlet port 221 and concave portion 212a that are arranged side by side in the direction in which second flow path 220 extends constitute a so-called muffler-type silencer. Also, the cross-sectional area of second inlet port 221 that is orthogonal to the air flowing direction is formed smaller than the cross-sectional area of concave portion 212a that is orthogonal to the air flowing direction. Second inlet port 221 is disposed downstream from concave portion 212a in the air flowing direction. Thus, similar to the above-mentioned first silencer 150, the above-mentioned section is also effective at reducing a noise, and consequently, can suppress leakage of the noise from CPAP apparatus 1A.

It should be noted that the cross-sectional area of second inlet port 221 that is orthogonal to the air flowing direction is suitably equal to or less than the half of the cross-sectional area of concave portion 212a that is orthogonal to the air flowing direction. This configuration can effectively suppress leakage of the noise through second inlet port 221.

The above-mentioned concave portion does not necessarily need to be provided in stage surface 212 of second housing 210, but may be provided in the portion of the outer surface of first housing 110 that includes a position that faces second inlet port 221 (i.e., a part of mounting surface 112) or may be provided in both stage surface 212 and mounting surface 112.

On the other hand, as shown in FIGS. 9 and 12, in the state where base unit 200 is attached to main body unit 100, first connection surface 113 of first housing 110 and second connection surface 213 of second housing 210 are disposed to face each other. Thereby, first inlet port 121 provided in first connection surface 113 is connected to second outlet port 222 provided in second connection surface 213 while first outlet port 122 provided in first connection surface 113 is connected to third inlet port 231 provided in second connection surface 213.

In this case, as shown in FIG. 2 mentioned above, second connection surface 213 of second housing 210 is provided with a gasket 217 so as to surround second outlet port 222. In the state where base unit 200 is attached to main body unit 100, gasket 217 is compressed by first housing 110 and second housing 210 so as to come into close contact with first housing 110 and second housing 210.

By the configuration as described above, in the first use state where the CPAP apparatus is used in the state where base unit 200 is attached to main body unit 100, gasket 217 compressed to surround first inlet port 121 and second outlet port 222 is disposed. This can prevent leakage of air through the connection portion between second outlet port 222 and first inlet port 121, and also can suppress leakage of noise through this connection portion to the outside.

Furthermore, second connection surface 213 of second housing 210 is provided with a gasket 218 so as to surround third inlet port 231. In the state where base unit 200 is attached to main body unit 100, gasket 218 is compressed by first housing 110 and second housing 210 so as to come into close contact with first housing 110 and second housing 210.

By the configuration as described above, in the first use state where the CPAP apparatus is used in the state where base unit 200 is attached to main body unit 100, gasket 218 compressed so as to surround first outlet port 122 and third inlet port 231 is disposed. This can prevent leakage of air through the connection portion between first outlet port 122 and third inlet port 231, and also can suppress leakage of noise through this connection portion to the outside.

The above-mentioned gasket does not necessarily need to be provided on second connection surface 213 of second housing 210, but may be provided on first connection surface 113 of first housing 110. In this case, it is preferable to provide the gasket so as to surround each of first inlet port 121 and first outlet port 122.

As shown in FIGS. 9 to 12, third flow path 230 and humidifying mechanism 250 are provided in the space inside second chamber 216. Third flow path 230 is provided so as to connect third inlet port 231 provided in second connection surface 213 of second housing 210 to third outlet port 232 provided in tube connection surface 211 of second housing 210. Humidifying mechanism 250 is placed on third flow path 230.

In this case, third flow path 230 is separated by the above-mentioned partition wall 214 from second flow path 220. Humidifying mechanism 250 is also separated by the above-mentioned partition wall 214 from second silencer 240. In other words, second silencer 240 and humidifying mechanism 250 are disposed side by side in the horizontal direction on the bottom plate portion that forms the mounting surface of second housing 210.

Humidifying mechanism 250 includes a tank 251 that stores water 253, and a so-called heating-type humidifying device formed of a heater and the like (not shown). Tank 251 can be attached to second housing 210 in an attachable and detachable manner. When water 253 is consumed and the water storage amount decreases, tank 251 can be detached from second housing 210, and filled with water 253, and then again attached to second housing 210.

The upper portion of tank 251 is provided with an inflow path 252 through which air introduced into second housing 210 is guided. Thereby, the air introduced into second housing 210 through third inlet port 231 provided in second connection surface 213 of second housing 210 flows through inflow path 252 into the upper space of water 253 stored in tank 251. When the air flows through the space, steam generated in humidifying mechanism 250 is applied to the air. The space and inflow path 252 correspond to third flow path 230.

As shown in FIG. 9, the wall portion (i.e., the top plate portion) that forms tube connection surface 211 of second housing 210 is provided with third outlet port 232. Third outlet port 232 has a nozzle shape so as to allow air tube 300 to be connected thereto.

Thus, in the first use state, the air suctioned from second inlet port 221 flows through second flow path 220, first flow path 120, and third flow path 230 sequentially in this order so as to be discharged from third outlet port 232, as described above. More specifically, the air suctioned from second inlet port 221 first flows through second flow path 220 provided in first chamber 215 of second housing 210, then flows through first flow path 120 that is formed of wide portion 115, narrow portion 116, air blower chamber 117, air blower 140, and hose 160 provided in first housing 110, and further flows through third flow path 230 provided in second chamber 216 of second housing 210 so as to be discharged from third outlet port 232.

In CPAP apparatus 1A according to the present embodiment as described above, the above-mentioned configuration is provided to allow two types of use states including: the first use state where CPAP apparatus 1A is used in the state where main body unit 100 is attached to base unit 200; and the second use state where CPAP apparatus 1A is used in the state where main body unit 100 is not attached to base unit 200, as repeatedly stated above.

Thus, for example, during staying at home and the like, CPAP apparatus 1A is used in the state where base unit 200 is attached to main body unit 100 to thereby allow high quietness. On the other hand, for example, during staying out overnight and the like, base unit 200 does not have to be carried but only main body unit 100 needs to be carried, thereby allowing high portability.

In this case, second silencer 240 provided in base unit 200 is greater in volume occupied in CPAP apparatus 1A than first silencer 150 provided in main body unit 100. In general, a silencer is improved in silencing effect in the entire frequency band in proportion to its occupying volume. Thus, as the occupying volume of second silencer 240 is larger, second silencer 240 can achieve a higher silencing effect, but the apparatus is increased in size accordingly.

However, as described above, second silencer 240 is provided not in main body unit 100 but in base unit 200. Thereby, during staying out overnight and the like, CPAP apparatus 1A can be used in the above-mentioned second use state during bedtime and during sleep while carrying main body unit 100 but not carrying base unit 200. Also, during staying at home and the like, CPAP apparatus 1A can be used in the above-mentioned first use state during bedtime and during sleep in the state where base unit 200 is attached to main body unit 100.

Therefore, a high silencing effect during staying at home and the like can be achieved while improving the portability for staying out overnight and the like, thereby allowing a user-friendly CPAP apparatus that can be highly convenient not only during staying at home and the like but also during staying out overnight and the like.

Second Embodiment

Figure 13:
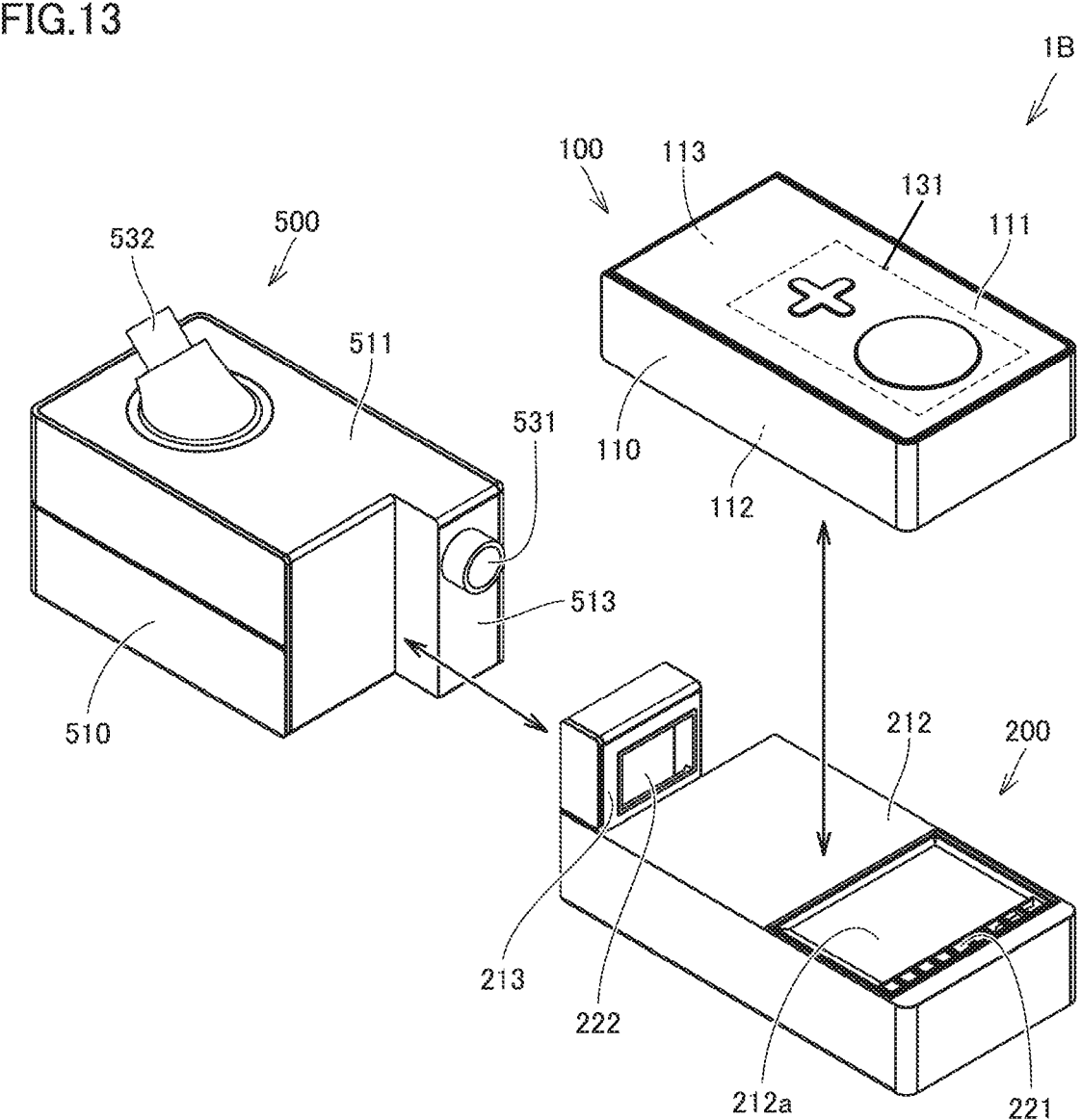
FIG. 13 is a perspective view showing the manner of attachment and detachment of a main body unit, a base unit and an additional base unit of a CPAP apparatus according to the second embodiment.

FIG. 13 is a perspective view showing the manner of attachment and detachment between a main body unit, a base unit, and an additional base unit of a CPAP apparatus according to the second embodiment of the present disclosure. In the following, a CPAP apparatus 1B according to the second embodiment will be described with reference to FIG. 13.

As shown in FIG. 13, CPAP apparatus 1B includes a main body unit 100 as the first unit, a base unit 200 as the second unit, and an additional base unit 500 as the third unit.

Main body unit 100 is the same as that in the above-mentioned first embodiment. On the other hand, base unit 200 is different from that in the above-mentioned first embodiment and mainly includes second flow path 220 and second silencer 240, but does not include third flow path 230 and humidifying mechanism 250. Furthermore, additional base unit 500 mainly has a third flow path 530 and a humidifying mechanism 550.

In other words, CPAP apparatus 1B according to the present embodiment is configured of two units (i.e., base unit 200 and additional base unit 500 in the present embodiment) obtained by dividing base unit 200 in CPAP apparatus 1A according to the first embodiment by the above-mentioned partition wall 214. The configuration other than the above is basically the same as that of CPAP apparatus 1A according to the above-described first embodiment.

Base unit 200 is attachable to and detachable from main body unit 100. Furthermore, additional base unit 500 is also attachable to and detachable from main body unit 100. In this case, CPAP apparatus 1B according to the present embodiment is configured to be usable in the following four states including: the state where both base unit 200 and additional base unit 500 are attached to main body unit 100; the state where base unit 200 is attached to main body unit 100, but additional base unit 500 is not attached to main body unit 100; the state where additional base unit 500 is attached to main body unit 100, but base unit 200 is not attached to main body unit 100; and the state where both base unit 200 and the additional base unit are not attached to main body unit 100.

Second housing 210 of base unit 200 has stage surface 212 provided with second inlet port 221 and second connection surface 213 provided with second outlet port 222. Also, a third housing 510 of additional base unit 500 has a third connection surface 513 provided with a third inlet port 531, and a tube connection surface 511 provided with a third outlet port 532.

Thereby, in the state where base unit 200 and additional base unit 500 are attached to main body unit 100, mounting surface 112 of first housing 110 is located to face stage surface 212 of second housing 210 while first connection surface 113 of first housing 110 is located to face second connection surface 213 of second housing 210 and third connection surface 513 of third housing 510. Accordingly, first inlet port 121 and first outlet port 122 provided in first connection surface 113 of first housing 110 are to be respectively connected to second outlet port 222 provided in second connection surface 213 of second housing 210 and third inlet port 231 provided in third connection surface 513 of third housing 510.

On the other hand, in the state where base unit 200 is attached to main body unit 100 but additional base unit 500 is not attached to main body unit 100, mounting surface 112 of first housing 110 is located to face stage surface 212 of second housing 210 while first connection surface 113 of first housing 110 is located to face second connection surface 213 of second housing 210. Accordingly, first inlet port 121 provided in first connection surface 113 of first housing 110 is to be connected to second outlet port 222 provided in second connection surface 213 of second housing 210.

On the other hand, in the state where additional base unit 500 is attached to main body unit 100 but base unit 200 is not attached to main body unit 100, first connection surface 113 of first housing 110 is located to face third connection surface 513 of third housing 510. Accordingly, first outlet port 122 provided in first connection surface 113 of first housing 110 is to be connected to third inlet port 531 provided in third connection surface 513 of third housing 510.

Furthermore, in the state where base unit 200 and additional base unit 500 are not attached to main body unit 100, first connection surface 113 of first housing 110 is exposed to the outside. Thus, each of first inlet port 121 and first outlet port 122 that are provided in first connection surface 113 of first housing 110 is opened to the outside.

In addition to the first use state and the second use state as described above, the configuration as described above allows implementation of: the third use state where the CPAP apparatus is used in the state where base unit 200 is attached to main body unit 100, but additional base unit 500 is not attached to main body unit 100; and the fourth use state where the CPAP apparatus is used in the state where additional base unit 500 is attached to main body unit 100 but base unit 200 is not attached to main body unit 100. Accordingly, in the third use state, second silencer 240 is added to thereby improve the silencing effect. In the fourth use state, humidifying mechanism 250 is added, so that moisture can be added to the air that is to be fed into a respiratory tract.

Therefore, by CPAP apparatus 1B according to the present embodiment, the effects described in the above first embodiment can be achieved, and additionally, the apparatus can be used in the use state arbitrarily selected from among the above-mentioned four use states, with the result that a further user-friendly CPAP apparatus can be provided.

Third Embodiment

Figure 14:
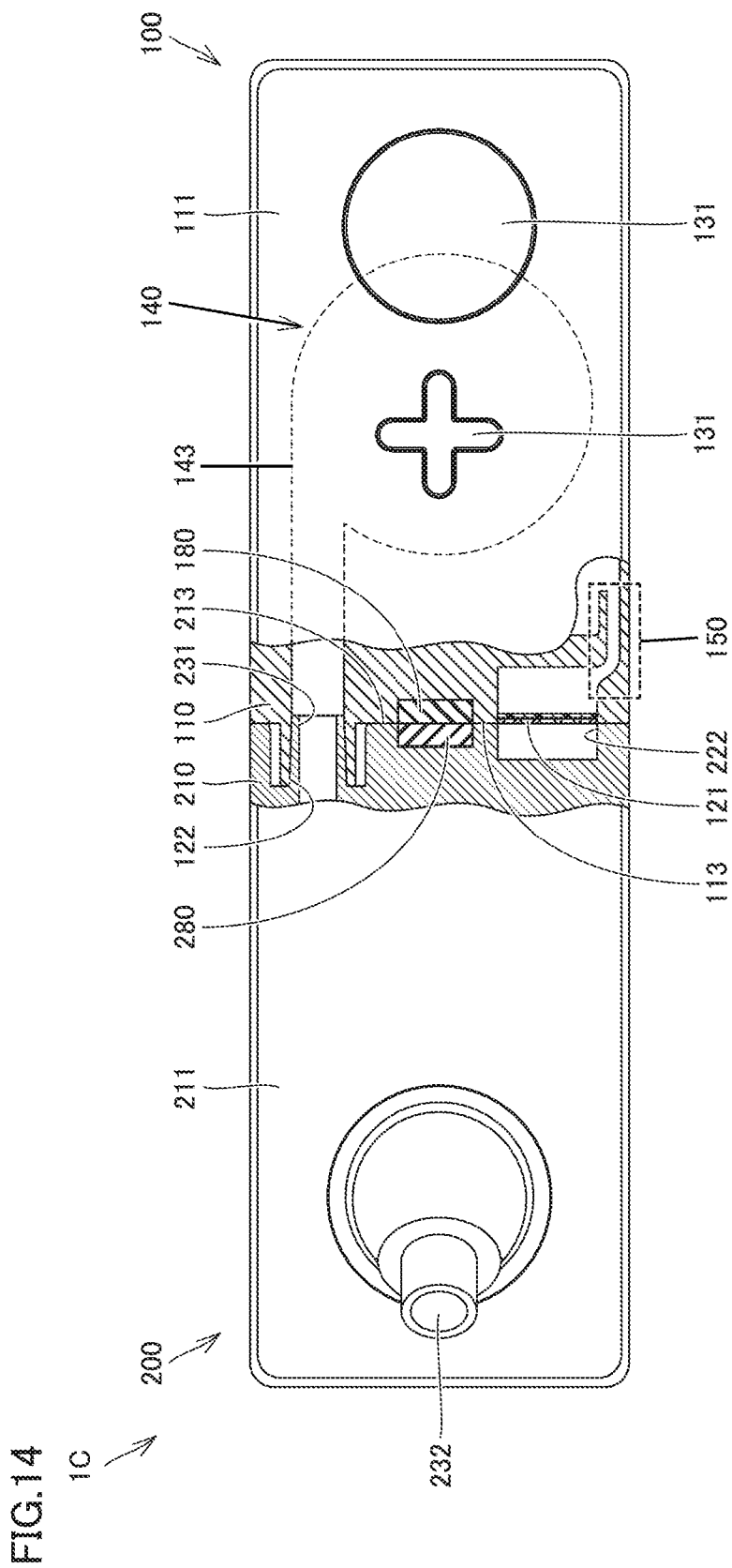
FIG. 14 is a partially cutaway plan view showing the state where a main body unit is attached to a base unit in a CPAP apparatus according to the third embodiment.

FIG. 14 is a partially cutaway plan view showing the state where a main body unit is attached to a base unit in a CPAP apparatus according to the third embodiment of the present disclosure. In the following, a CPAP apparatus 1C according to the present embodiment will be described with reference to FIG. 14.

As shown in FIG. 14, CPAP apparatus 1C has basically the same configuration as that in the above-described first embodiment, and includes main body unit 100 as the first unit and base unit 200 as the second unit. Main body unit 100 includes air blower 140 and first silencer 150. Base unit 200 includes a second silencer (that is the same as second silencer 240 shown in FIG. 11 and the like) and a humidifying mechanism (that is the same as humidifying mechanism 250 shown in FIG. 9 and the like).

In this case, although no details will be explained for avoiding repeated explanations, CPAP apparatus 1C according to the present embodiment can also take two types of use states including: the first use state where CPAP apparatus 1C is used in the state where main body unit 100 is attached to base unit 200; and the second use state where CPAP apparatus 1C is used in the state where main body unit 100 is not attached to base unit 200, as in the above-described first embodiment. One of these two types of use states can be selected when CPAP apparatus 1C is used. Therefore, a user-friendly CPAP apparatus that is excellent in portability and quietness can be provided.

Furthermore, CPAP apparatus 1C according to the third embodiment allows ease of the operation of attaching and detaching base unit 200 to and from main body unit 100. In other words, in CPAP apparatus 1C, a first magnet 180 is provided in first connection surface 113 of first housing 110 included in main body unit 100, and a second magnet 280 is provided in second connection surface 213 of second housing 210 included in base unit 200. These first magnet 180 and second magnet 280 are attracted to and repelled from each other by the magnetic force, thereby allowing ease of the above-mentioned attachment and detachment operations.

In this case, first magnet 180 and second magnet 280 each may be a permanent magnet or may be an electromagnet. In the case where one or both of first magnet 180 and second magnet 280 is or are an electromagnet, the electromagnet can be switched to be turned ON and OFF by a user interface such as a switch separately provided in CPAP apparatus 1C. In addition, first magnet 180 and second magnet 280 may be disposed to face each other in the state where base unit 200 is attached to main body unit 100, and may be located to be exposed from the surface of the housing or may be located inside the housing.

For example, in the case where first magnet 180 is formed of an electromagnet while second magnet 280 is formed of a permanent magnet, the polarities of these magnets can be set so as to implement the following manner of attachment and detachment.

Firstly, when base unit 200 is attached to main body unit 100, first magnet 180 formed of an electromagnet is switched to an OFF state. Thereby, first magnet 180 functions simply as a metal member (e.g., a ferromagnetic body), and the magnetic force of second magnet 280 generates force that acts in the attachment direction between first magnet 180 and second magnet 280.

On the other hand, when base unit 200 is detached from main body unit 100, first magnet 180 formed of an electromagnet is switched to an ON state. Thereby, first magnet 180 functions as a magnet, and repulsion occurs between the magnetic force of first magnet 180 and the magnetic force of second magnet 280, thereby generating force that acts in the detachment direction between first magnet 180 and second magnet 280.

Thereby, first magnet 180 and second magnet 280 act against each other, which generates attracting force or repelling force between main body unit 100 and base unit 200 in the attachment and detachment operation, thereby allowing ease of the mounting operation. Particularly in the attachment operation, the above-mentioned attracting force is caused only by roughly aligning the projections and recesses provided in main body unit 100 with the projections and recesses provided in base unit 200. This force allows accurate positioning of base unit 200 with respect to main body unit 100, thereby allowing further ease of the attachment operation.

Furthermore, for example, in the case where first magnet 180 is formed of a permanent magnet and second magnet 280 is formed of an electromagnet, the polarities of these magnets can be set so as to implement the following manner of attachment and detachment.

Firstly, when base unit 200 is attached to main body unit 100, second magnet 280 formed of an electromagnet is switched to an OFF state. Thereby, second magnet 280 functions simply as a metal member (a ferromagnetic body), and the magnetic force of first magnet 180 generates force that acts in the attachment direction between first magnet 180 and second magnet 280.

On the other hand, when base unit 200 is detached from main body unit 100, second magnet 280 formed of an electromagnet is switched to an ON state. Thereby, second magnet 280 functions as a magnet, and repulsion occurs between the magnetic force of second magnet 280 and the magnetic force of first magnet 180, thereby generating force that acts in the detachment direction between first magnet 180 and second magnet 280.

Thereby, first magnet 180 and second magnet 280 act against each other, which generates attracting force or repelling force between main body unit 100 and base unit 200 in the attachment and detachment operation, thereby allowing ease of the mounting operation. Particularly in the attachment operation, the above-mentioned attracting force is caused only by roughly aligning the projections and recesses provided in main body unit 100 with the projections and recesses provided in base unit 200. This force allows accurate positioning of base unit 200 with respect to main body unit 100, thereby allowing further ease of the attachment operation.

In this case, the positions in which first magnet 180 and second magnet 280 are disposed are not limited to the positions as shown in FIG. 14, but may be positions as described below.

For example, first magnet 180 may be provided at or near first outlet port 122 of first housing 110, and second magnet 280 may be provided at or near third inlet port 231 of second housing 210. In this case, first magnet 180 and second magnet 280 may be disposed annularly so as to surround the flow path through which air flows in the attached state (i.e., first flow path 120 and third flow path 230). Further, in this case, a plurality of magnets obtained by dividing first magnet 180 and second magnet 280 may be arranged annularly. In the configuration as described above, first outlet port 122 and third inlet port 231 are easily aligned with each other particularly during attachment, and further, the sealing performance in the connection portion therebetween is also improved.

Furthermore, for example, first magnet 180 may be provided at or near first inlet port 121 of first housing 110, and second magnet 280 may be provided at or near second outlet port 222 of second housing 210. In this case, first magnet 180 and second magnet 280 may be disposed in a frame shape so as to surround the flow path through which air flows in the attached state (i.e. first flow path 120 and second flow path 220). Further, in this case, a plurality of magnets obtained by dividing first magnet 180 and second magnet 280 may be arranged in a frame shape. In the configuration as described above, first inlet port 121 and second outlet port 222 are easily aligned with each other particularly during attachment, and further, the sealing performance in the connection portion therebetween is also improved.

In addition, one of first magnet 180 and second magnet 280 mentioned above may be replaced with an electromagnet or a permanent magnet so as to be formed of a metal member (a ferromagnetic body). Also, in such a case, the magnetic force acts to allow ease of the attachment operation and accurate positioning during this attachment operation. Also, in the detachment operation, base unit 200 only needs to be detached from main body unit 100 against this magnetic force.

The above first to third embodiments of the present disclosure have been described while exemplifying the case where a so-called muffler type silencer formed of a wide portion and a narrow portion arranged side by side in the first flow path is applied as the first silencer provided in the main body unit as the first unit, but the first silencer is not limited thereto. The first silencer may be conventionally known various types of silencers or may be a combination thereof. It should be noted that a smaller-sized silencer is desirable in consideration of the portability for staying out overnight and the like.

Furthermore, the above first to third embodiments of the present disclosure have been described while exemplifying the case where a silencer configured to include a resonant tube is applied as the second silencer provided in the base unit as the second unit, but the second silencer is not limited thereto. The second silencer may be conventionally known various types of silencers or may be a combination thereof.

It should be noted that the above-mentioned cross-sectional areas of various types of flow paths and the like can be obtained from the cross-sectional image acquired by a computed tomography (CT) inspection using X rays, and the like, for example, without division or disassembly of the CPAP apparatus itself. Furthermore, the cross-sectional area can also be obtained, as a matter of course, by directly observing a plurality of portions obtained by dividing or disassembling the CPAP apparatus.

It should be understood that the embodiments disclosed herein are illustrative and non-restrictive in every respect. The technical scope of the present disclosure is defined by the terms of the claims, and is intended to include any modifications within the meaning and scope equivalent to the terms of the claims.

REFERENCE SIGNS LIST 1A, 1B, 1C CPAP apparatus, 100 main body unit, 110 first housing, 111 operation surface, 112 mounting surface 112a leg, 113 first connection surface, 114 separation wall, 115 wide portion, 116 narrow portion, 117 air blower chamber, 120 first flow path, 120A upstream-side flow path portion, 120B downstream-side flow path portion, 121 first inlet port, 122 first outlet port, 130 control unit, 131 operation unit, 132 flow rate sensor, 133 pressure sensor, 140 air blower, 141 impeller, 142 drive motor, 143 casing, 144 intake port, 145 discharge port, 150 first silencer, 160 hose, 170 filter, 171 filter cover, 180 first magnet, 200 base unit, 210 second housing, 211 tube connection surface, 212 stage surface 212a concave portion, 213 second connection surface, 214 partition wall, 215 first chamber, 216 second chamber, 217,218 gasket, 219 third connection surface, 220 second flow path, 221 second inlet port, 222 second outlet port, 230 third flow path, 231 third inlet port, 232 third outlet port, 240 second silencer, 241 resonant tube, 250 humidifying mechanism, 251 tank, 252 inflow path, 253 water, 280 second magnet, 300 air tube, 400 mask, 500 additional base unit, 510 third housing, 511 tube connection surface, 513 third connection surface, 530 third flow path, 531 third inlet port, 532 third outlet port, 550 humidifying mechanism.

The invention claimed is:

1. A continuous positive airway pressure (CPAP) apparatus that feeds air suctioned into the CPAP apparatus to a respiratory tract of a user, the CPAP apparatus comprising:
   a first unit including an air blower and a first housing in which the air blower is housed; and
   a second unit including a second housing and being attachable to and detachable from the first unit, wherein
   the first housing comprises:
      a first inlet port through which air is introduced from outside the first housing,
      a first outlet port through which air is discharged from inside the first housing, and
      a first flow path in which the air blower is provided and that connects the first inlet port and the first outlet port,
   the second housing comprises:
      a second inlet port through which air is introduced from outside the second housing,
      a second outlet port through which air is discharged from inside the second housing, and
      a second flow path that connects the second inlet port and the second outlet port, the second unit further includes a silencer provided in the second flow path,
   in a first use state of the CPAP apparatus where the second unit is attached to the first unit, the second outlet port is connected to the first inlet port, and
   in a second use state of the CPAP apparatus where the second unit is not attached to the first unit, the first inlet port is opened to outside.

2. The CPAP apparatus according to claim 1, wherein the silencer includes a resonant tube that is branched from the second flow path.

3. The CPAP apparatus according to claim 1, wherein the first housing or the second housing is provided with a gasket so as to surround each of the first inlet port and the second outlet port in the first use state.

4. The CPAP apparatus according to claim 1, wherein the second inlet port is provided in a portion of the second housing that faces the first housing at a distance from the first housing in the first use state.

5. The CPAP apparatus according to claim 4, wherein the second inlet port is disposed at an outer surface of the second housing, and a concave portion is disposed at an outer surface of the first housing at a position faces the second inlet port, the concave portion being recessed from a surrounding area.

6. The CPAP apparatus according to claim 1, wherein the second housing further comprises:
   a third inlet port through which air is introduced from outside the second housing,
   a third outlet port through which air is discharged from inside the second housing, and
   a third flow path that connects the third inlet port and the third outlet port,
   the second unit further includes a humidifying mechanism provided in the third flow path, and
   the third inlet port is connected to the first outlet port in the first use state.

7. The CPAP apparatus according to claim 6, wherein the first housing comprises:
   a mounting surface located vertically on a lower side in the first use state, and
   a first connection surface provided with the first inlet port and the first outlet port,
   the second housing includes a bottom plate portion disposed vertically on a lower side in the first use state,
   the silencer and the humidifying mechanism are disposed side by side in a horizontal direction on the bottom plate portion in the first use state,
   the second housing comprises:
      a stage surface located vertically above the silencer in the first use state,
      an upper surface located vertically above the humidifying mechanism and located higher than the stage surface in the first use state, and
      a second connection surface connecting the stage surface and the upper surface and provided with the second outlet port and the third inlet port, and
   the second unit is attached to the first unit such that the mounting surface faces the stage surface, and the first connection surface faces the second connection surface, so as to connect the second outlet port to the first inlet port and to connect the third inlet port to the first outlet port.

8. The CPAP apparatus according to claim 1, further comprising a third unit that includes a third housing and that is attachable to and detachable from the first unit, wherein the third housing comprises:
   a third inlet port through which air is introduced from outside the third housing,
   a third outlet port through which air is discharged from inside the third housing, and
   a third flow path that connects the third inlet port and the third outlet port,
   the third unit further includes a humidifying mechanism provided in the third flow path, and
   the third inlet port is connected to the first outlet port in the first use state.

* * * * *